United States Patent [19]

Lang et al.

[11] 4,235,918

[45] Nov. 25, 1980

[54] BENZENESULFONAMIDE DERIVATIVES AND PROCESSES FOR THEIR MANUFACTURE

[75] Inventors: Hans-Jochen Lang, Hofheim; Roman Muschaweck; Max Hropot, both of Frankfurt am Main, all of Fed. Rep. of Germany

[73] Assignee: Hoechst Aktiengesellschaft, Frankfurt am Main, Fed. Rep. of Germany

[21] Appl. No.: 934,063

[22] Filed: Aug. 16, 1978

[30] Foreign Application Priority Data

Aug. 18, 1977 [DE] Fed. Rep. of Germany ....... 2737195

[51] Int. Cl.$^2$ ................. C07D 207/26; C07C 143/78; A61K 31/40; A61K 31/18
[52] U.S. Cl. ............................ 424/274; 260/326.5 SF; 260/326.25; 260/326.41; 260/340.7 260/340.9 R; 424/321; 424/267; 424/278; 546/208; 546/233; 564/88
[58] Field of Search ................. 260/326.5 SF, 326.25, 260/556 C, 340.7, 340.9 R, 326.41, 326.5 S; 424/321, 274, 278, 267; 546/208, 233, 234

[56] References Cited

U.S. PATENT DOCUMENTS

| | | | |
|---|---|---|---|
| 3,947,460 | 3/1976 | Houlihan | 260/326.5 FL |
| 4,061,647 | 12/1977 | Lang et al. | 260/306.7 T |
| 4,061,761 | 12/1977 | Lang et al. | 424/270 |
| 4,083,979 | 4/1979 | Lang et al. | 424/251 |
| 4,118,501 | 10/1978 | Lang et al. | 424/270 |
| 4,125,614 | 11/1978 | Lang et al. | 424/251 |
| 4,129,656 | 12/1978 | Lang et al. | 424/263 |

OTHER PUBLICATIONS

Von E. Jucker et al., Arzneimittel-Forsch, 13,269 (1963).

*Primary Examiner*—Jose Tovar
*Attorney, Agent, or Firm*—Curtis, Morris & Safford

[57] ABSTRACT

Benzenesulfonamide derivatives as defined in the specification have an outstanding salidiuretic action. Some of the compounds exhibit a significant increase in the excretion of uric acid and the uric acid clearance. They are distinguished by a long-lasting period of action and are suitable for the treatment of hypertonic conditions in humans, optionally in combination with anti-hypertonic agents.

14 Claims, No Drawings

BENZENESULFONAMIDE DERIVATIVES AND PROCESSES FOR THEIR MANUFACTURE

The invention relates to benzenesulfonamide derivatives of the general formula I

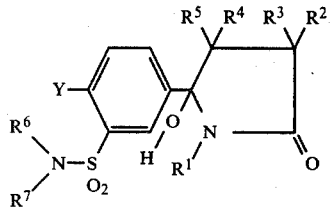

wherein $R^1$ denotes hydrogen, alkyl or alkenyl with 1 to 4 C atoms, it also being possible for the alkyl radical to carry a methoxy group, cycloalkyl with 3 to 5 ring members or benzyl, $R^2$ to $R^6$ denote hydrogen or an alkyl radical with 1 to 4 C atoms, $R^7$ denotes hydrogen, alkyl with 1 to 10 C atoms, it also being possible for the alkyl radical to carry 1 or 2 methoxy or ethoxy groups or an ethylenedioxy or propylenedioxy group, alkenyl with 3 to 5 C atoms, cycloalkyl with 3 to 12 ring members, which is optionally substituted by a methyl group, cycloalkylalkyl with 5 or 6 ring members and with 1 or 2 C atoms in the alkyl part, phenylalkyl with 1 to 2 C atoms in the alkyl part, it being possible for the phenyl radical to be monosubstituted or disubstituted and to carry methyl, methoxy or chlorine as substituents, or $R^6$ and $R^7$, together with the N atom, also denote a saturated 5-membered to 6-membered heterocyclic ring and Y denotes halogen, hydrogen, trifluoromethyl or methyl, and the open-chain tautomeric forms, corresponding to I, of the formula Ia

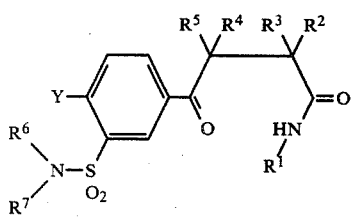

wherein $R^1$ and $R^7$ and Y have the meaning indicated.

The invention furthermore relates to a process for the manufacture of the compounds of the general formula I, which comprises (a) reacting compounds of the general formula II

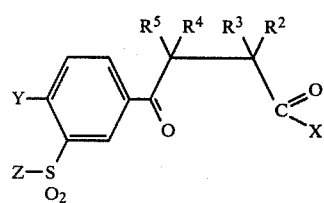

wherein Z denotes a halogen atom or the group $NR^6R^7$, X denotes a leaving group and $R^2$ to $R^7$ and Y have the meaning indicated in claim 1, with an amine of the formula III

wherein $R^1$ has the meaning indicated in claim 1 and $R^8$ denotes hydrogen or a benzyl or diphenylmethyl radical, which can be optionally substituted by methoxy groups, and, if $R^8$ does not denote hydrogen, subjecting the resulting compounds to hydrogenolysis or hydrolysis, or (b) treating compounds of the general formula IV

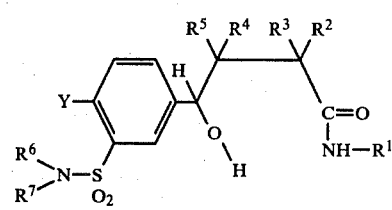

wherein $R^1$ to $R^7$ and Y have the meaning indicated, with an oxidizing agent, or (c) reacting compounds of the general formula V

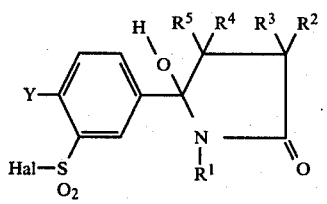

wherein Y and $R^1$ to $R^5$ have the above meaning and Hal represents halogen, with ammonia or an amine of the general formula VI

wherein $R^6$ and $R^7$ have the meaning indicated, or (d) reacting compounds of the general formula VII

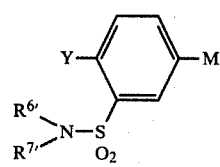

wherein M represents Li or MgHal, Y has the above meaning, but does not represent bromine or iodine, and $R^{6'}$ and $R^{7'}$ have the meaning of $R^6$ and $R^7$, with the exception of hydrogen, or represent a metal cation, with succinimide derivatives of the general formula VIII

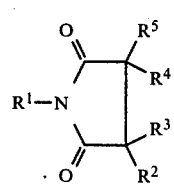

wherein R[1] to R[5] have the meaning indicated, and subsequently treating the resulting compounds with an acid, or (e) reacting compounds of the general formula IX

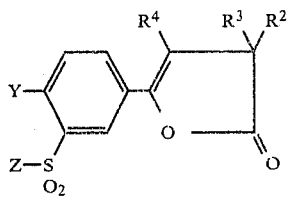

wherein R[1] to R[4], Z and Y have the meaning indicated, with an amine of the formula III, and optionally alkylating compounds of the general formula I, wherein R[6] and/or R[7] denote hydrogen, obtained by routes (a) to (e).

The compounds of the formula I and V can also exist in their open-chain tautomeric forms (Ia) and (Va):

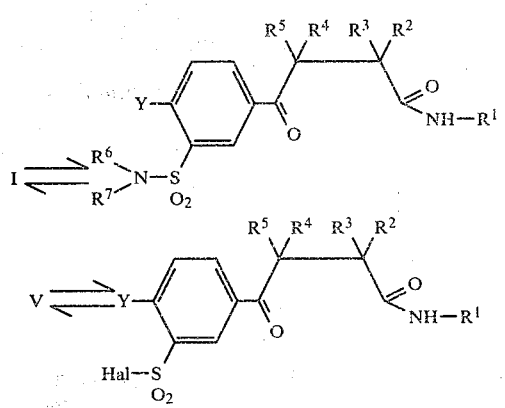

Both the possible tautomeric forms are indicated in the embodiment examples.

The compounds of the formula I according to the invention can also have their geometric isomeric structures.

The alkyl and alkenyl radicals in the substituents R[1] to R[7] can be either straight-chain or branched.

In the compounds of the formula II used as starting materials for procedure (a), X as a leaving group denotes, for example, halogen, in particular chlorine, an alkoxy or optionally substituted phenoxy radical, a nitrile or azide group or an activated ester radical, such as the cyanomethoxy radical —OCH$_2$CN. However, the radical of a mixed anhydride is particularly advantageous.

These compounds II are manufactured in the customary manner from the carboxylic acids corresponding to the formula II (X=OH). The mixed anhydrides are obtained by reacting corresponding carboxylic acid salts (X in formula II is, for example, ONa, OK, O-trialkylammonium) with an activated acid derivative. Examples of compounds which are used for this are an alkyl chloroformate, preferably ethyl chloroformate or methyl chloroformate, a carbamoyl chloride, such as, for example, N,N-dimethylcarbamoyl chloride or N,N-diethylcarbamoyl chloride, or the acid chloride of an aromatic or aliphatic sulfonic acid, such as, for example, methanesulfonyl, ethanesulfonyl, benzenesulfonyl or p-toluenesulfonyl chloride. The reaction to give the mixed anhydride is advantageously carried out, for example, at $-30°$ C. to $+30°$ C. in an anhydrous polar organic solvent, such as, for example, acetone, methyl ethyl ketone, ethyl acetate, dimethylformamide, dimethylacetamide, dimethylsulfoxide, acetonitrile or a lower aliphatic alcohol or, preferably, in tetrahydrofuran, dioxan, ethylene glycol dimethyl ether or corresponding glycol ethers.

Although it is possible to isolate the mixed anhydrides, for example by evaporating off the solvent at temperatures between $-50°$ and $+10°$ C. and extracting the anhydrides from the residue, for example with ethyl acetate, it is advantageous to add the amine of the general formula III to the reaction mixture without isolating the mixed anhydride. The amine can be added undiluted or in one of the solvents mentioned, and it is also possible to used aqueous solutions of the amine or of ammonia. At least 1 mole, but advantageously an excess (10-fold and more), of amine is used here. The reaction is carried out in a temperature range between $-30°$ C. and $+100°$ C., preferably between $+5°$ C. and $+40°$ C. The reaction time is between 10 minutes and 5 days, and the reaction is appropriately followed by thin layer chromatography, advantageously on silica gel.

In principle, the acid chlorides of the formula II, wherein X represents chlorine, which can be prepared from the carboxylic acids of the formula II (X=OH) with COCl$_2$, oxalyl chloride, POCl$_3$, SOCl$_2$, PCl$_3$ or PCl$_5$, are reacted with an amine of the formula III in the same manner as the mixed anhydrides.

If X in compounds of the general formula II denotes a lower alkoxy group with 1 to 6 C atoms, preferably 1-4 C atoms, or a phenoxy radical which is optionally substituted by halogen, the reaction with an amine of the formula III is carried out in water or a polar organic solvent which is inert towards amines, for example in a lower alkanoic acid amide, such as dimethylformamide or dimethylacetamide, in dimethylsulfoxide or dimethyl sulfone or in a cyclic or open-chain ether or polyether, such as, for example, tetrahydrofuran, dioxan, ethylene glycol dimethyl ether, ethylene glycol diethyl ether, diethylene glycol dimethyl ether or diethylene glycol diethyl ether, but preferably in a lower alcohol, such as, for example, in methanol, ethanol, propanol or isopropanol, or in excess amine. The reaction is carried out within a temperature range from $0°$ C. to $120°$ C., preferably between $10°$ C. and $60°$ C. and in particular between $15°$ C. and $30°$ C. The course of the reaction is monitored by a thin layer chromatogram, for example on silica gel using methanol, ethyl acetate, toluene or mixtures of these solvents as the running agent. The reaction time is between 1 hour and 14 days, for example between 5 and 72 hours at room temperature. The carboxylic acid esters of the formula II and the amines of the formula III are preferably reacted in a molar ratio of 1:1 to 1:3; it is also possible to use the amine in an up to 10-fold molar excess.

The compounds of the formula II wherein X represents an alkoxy radical are obtained in the customary manner by reacting the carboxylic acid II (X=OH) with a lower alkanol with 1-6 C atoms, for example in the presence of an organic or inorganic acid chloride.

The corresponding acid cyanides, acid azides or activated esters of the formula II, in which X=CN, N$_3$ or —O—CH$_2$CN, can also be reacted with an amine of the formula III in the same manner as the esters.

After the aminolysis, the procedure during working up is advantageously to completely or partially remove solvent and excess amine under reduced pressure, to add water again if appropriate and to bring the mixture to a pH between 0 and 12, preferably between 5 and 10, with an organic or inorganic acid, such as HCl, acetic acid or ammonium chloride. The precipitate is filtered off, for which, if appropriate, it must first be crystallized out by customary operations, or is extracted with a suitable solvent, such as ethyl acetate, and the solution is dried and, after concentrating, the product is crystallized out.

The amines of the formula III are known from the literature. The carboxylic acids of the formula II, in which X=OH and wherein Z denotes a halogen atom (compare formula XIII) are obtained, for example, by subjecting an aromatic compound X to a Friedel-Crafts reaction with a succinic anhydride XI to give the compound XII

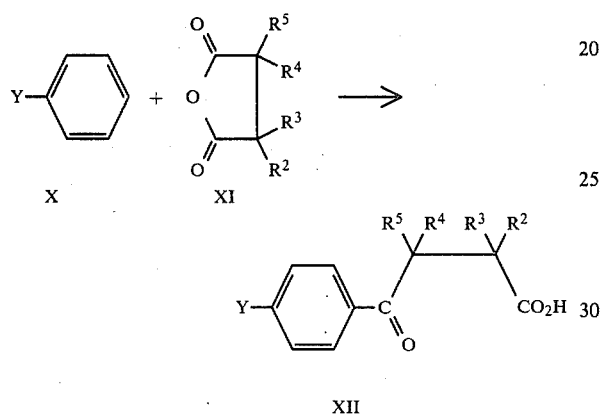

and by subsequent nitration, reduction, diazotization and a Merrwein reaction, compound XIII is obtained

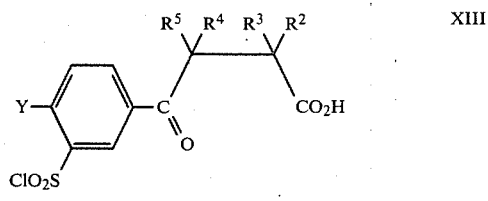

The conversion of the compound XIII into the corresponding sulfamoyl compound of the formula II (Z=NR$^6$R$^7$, X=OH) is achieved in the customary manner by reacting XIII with ammonia or an amine of the formulae III or NHR$^6$R$^7$.

If the reaction is carried out with an amine of the formula III in which R$^8$ does not denote hydrogen, the resulting compounds are then subjected to hydrolysis or hydrogenolysis. Hydrogenolysis is applied if R$^8$ denotes the benzyl radical. In this case, catalytic hydrogenation is effected in the customary manner. The hydrogenation is carried out at a temperature between 0° C. and 60° C., preferably between 10° C. and 30° C., with hydrogen gas under atmospheric pressure or slight excess pressure and advantageously using palladium, or preferably using palladium-on-animal charcoal, as the catalyst, the reaction being discontinued after the theoretical uptake of H$_2$ is achieved.

If R$^8$ denotes the diphenylmethyl radical or a substituted benzyl or diphenylmethyl radical which contains one or more methoxy groups in the nucleus, this radical is split hydrolytically, preferably acidolytically in an acid medium. "Cation trappers", preferably the equimolar amount of anisole, are added to the reaction mixture in order to prevent the formation of polymers or other side reactions. Trifluoroacetic acid or anhydrous liquid hydrogen fluoride is preferably used as the acid. The reaction is carried out between 0° and 70° C., preferably between 10° and 40° C., the reaction time being between 1 hour and 5 days. (Houben-Weyl, "Methoden der Organischen Chemie, Synthese von Peptiden Teil I" ("Methods of Organic Chemistry, Synthesis of Peptides, Part I"), 1974, pages 265 and 461–463). The mixture is worked up as above.

Preferred oxidizing agents which can be used according to procedure (b) are active manganese-IV oxide, iron-III salts, chromium-VI compounds or cerium-IV salts. Solvents which are used are halogenated hydrocarbons, such as, for example, methylene chloride, chloroform, tetrachloroethane and halogenated derivatives of benzene, such as chlorobenzene, fluorobenzene and benzotrifluoride, but preferably acetonitrile, the reaction being carried out at temperatures between 0° C. and 40° C., preferably between 20° C. and 30° C., over a period of 1 to 60 hours, preferably over a period of 6 to 36 hours.

The starting materials of the formula IV are obtained, for example, by splitting open lactones of the formula XIV

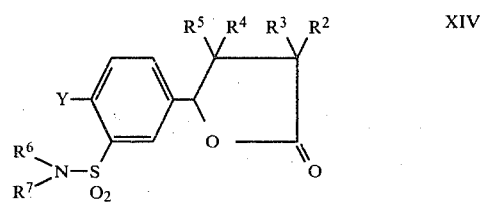

in the customary manner using amines of the formula III. this, 1 mole of the lactone is reacted with excess ammonia or amine III, optionally diluted in a polar solvent, preferably a lower alcohol, at a temperature between 20° and 200° C.

The lactones of the formula XIV are obtained, for example, from carboxylic acids of the formula II (X=OH and Z=NR$^6$R$^7$) by reduction with NaBH$_4$.

According to procedure (c) sulfonic acid chlorides of the general formula V are reacted with ammonia or an amine of the formula VI. Either aqueous solutions of ammonia and of the amines VI or liquid ammonia or pure amines, in excess, can be used for this, the excess ammonia or amine simultaneously functioning as the solvent. The reaction is also advantageously carried out in polar organic solvents, such as, for example, dimethylformamide, dimethylsulfoxide, dioxan, tetrahydrofuran or diethylene glycol dimethyl ether, but preferably in lower alcohols with 1–4 C atoms, such as, for example, in methanol, ethanol or isopropanol. At least 2 moles of ammonia or amine are used per mole of sulfochloride V, but a larger excess is advantageously used. It is also possible to use one mole of ammonia or amine VI if the reaction is carried out in the presence of an auxiliary base, about 1–6 molar equivalents of auxiliary base being used. Suitable auxiliary bases are organic or inorganic hydroxides, carbonates and bicarbonates, as well as salt solutions of weak organic and inorganic acids. Tertiary amines, such as, for example, triethylamine, tri-n-butylamine or ethyldicyclohexylamine, are particularly advantageous, and the reaction is optionally carried out in the presence of one of the solvents mentioned or a mixture thereof.

The reaction is carried out at temperatures between −30° and +80° C., preferably between +10° and +35° C. The reaction time is between 6 and 20 hours. The mixture is worked up as above.

The compounds of the formula V, in which Hal preferably represents chlorine, are manufactured from compounds of the formula XV wherein E denotes a nitro or amino group. Corresponding reactive carboxylic acid derivatives in which OH is replaced by X are reacted with amines of the formula III to give the compounds of the formula XVI

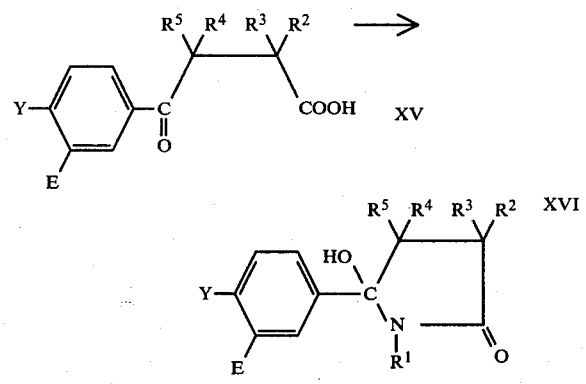

wherein E denotes a NO₂ or NH₂ group. If E denotes a NO₂ radical, it is reduced to the amino group. The sulfochlorides of the formula V are obtained from the amino compounds of the formula XVI by diazotization and a subsequent Meerwein reaction.

According to procedure (d), compounds of the formula VII, wherein R⁶ and R⁷ appropriately do not represent hydrogen, are reacted with succinimides of the general formula VIII. The compounds VII and VIII are advantageously reacted in the molar ratio 1:1 to 1:1.5 in an inert anhydrous solvent which is customary for metal-organic reactions. Cyclic or open-chain ethers or polyethers, such as, for example, diethyl ether, tetahydrofuran, dioxan, ethylene glycol dimethyl ether or diethylene glycol dimethyl ether, are preferably used as the solvent. The reaction is carried out in a temperaure range between 0° and 100° C., preferably between 15° and 50° C., and the reaction time is between 1 and 30 hours. Advantageously, a solution or suspension of 1 mole of the metal-organic compound VII is added in small portions to a solution of 1 to 1.5 moles of the compounds VIII in one of the solvents indicated. After the reaction has ended, the reaction products are hydrolyzed in a manner which is customary for metal-organic reactions, for example the reaction mixture is introduced into an aqueous, saturated solution of ammonium chloride at temperatures between −5° and +20 C., whilst maintaining the pH in the range from 6 to 9. Further working up of the compounds of the formula I thus obtained is carried out as described.

The compounds of the general formula VII are obtained in a manner which is customary for the preparation of metal-organic reagents, for example by reacting compounds of the formula VII wherein M denotes, for example, Br or I, with Li or magnesium or a metal-organic compound of the metals mentioned [Houben-Weyl, Methoden der Organischen Chemie (Methods of Organic Chemistry), 13/1 (1070), pages 134–159; volume 13/2a (1973), pages 54–162].

The compound of the formula VII in which M=Br is obtained, for example, from compounds of the general formula XVII

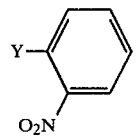

by bromination, and subsequent reduction of the nitro group. The resulting amino group is diazotized, the diazo group is sulfochlorinated by a Meerwein reaction and finally the product is reacted with an amine of the formula VI. The compounds of the formula VII wherein R⁶′ and/or R⁷′ denote a metal cation are obtained from the corresponding compounds VII in which R⁶′ and/or R⁷′=hydrogen and M=Br or I by reaction with a metal base, for example a metal hydroxide, or a metal-organic compound and subsequent metalation of bromine or I in the manner described above.

According to procedure (e), the process is advantageously carried out by reacting compounds of the general formula IX with amines of the formula III to give compounds of the formula I. The reaction conditions, that is to say reaction temperature, reaction time, reagents used and solvents, correspond to the above amine reactions. The compounds of the general formula IX are obtained from the carboxylic acids of the formula II (X=OH) by the action of an agent which splits off water, preferably thionyl chloride or acetic anhydride. If acetic anhydride is used, those compounds of the formula IX in which R⁶ and R⁷ do not represent hydrogen are preferred, in order to avoid undesired acylation.

The alkylation of the sulfonamide group in compounds of the general formula I wherein R⁶ and/or R⁷ denote hydrogen is carried out in the customary manner, for example by means of formaldehyde/formic acid, alkyl halides, dialkyl sulfate, alkyl tosylates or alkyl mesylates.

Compounds of the formula I wherein R¹ does not denote methyl are to be regarded as preferred if R⁶ and R⁷ represent hydrogen, especially if R² to R⁵ denote hydrogen.

Particularly preferred compounds are compounds of the formula I wherein R¹ denotes methyl and Y denotes chlorine or bromine, and of these, again, those compounds in which R² to R⁵ represent hydrogen are considered particularly preferred.

The process products are valuable medicaments and are distinguished by a very good diuretic and saluretic activity.

It is known that 4-(4-chloro-3-sulfamoylphenyl)-4-oxobutanoic acid and its methyl ester display a moderate salidiuretic activity in rats (Arzneimittel-Forsch. 13, 269 (1963)).

Furthermore, it is known that 1-alkyl-5-hydroxy-5-aryl-2-oxopyrrolidines, which carry no sulfonamide group on the aryl radical show stimulating actions on the central nervous system (German Offenlegungsschrift No. 2,453,356 and U.S. Pat. No. 3,947,460).

It was thus surprising that the amide derivatives I and Ia according to the invention have a very powerful salidiuretic action which is significantly superior, from a quantitative and qualitative point of view, to that of the known products listed. Moreover, in contrast to most medicaments having a salidiuretic action, some of the compounds according to the invention exhibit, in a unit dose of 50 mg/kg in rats treated with oxonate, a significant increase in the excretion of uric acid and the uric acid clearance, which is to be assessed as adadvantageous for therapeutic use.

The salidiuretic action of the new process products was determined in rats, using a unit dose of 50 mg/kg, administered orally. The products are superior in their activity to the salidiuretic activity of known commercial formulations of the thiazide group, such as, for example, of hydrochlorothiazide, and to that of chlorothalidone. Furthermore, the new process products are distinguished by a long-lasting period of action. The new process products are therefore particularly suitable for the treatment of hypertonic conditions in humans, for which they are optionally combined with an anti-hypertonic agent, as is generally customary at the present time.

Possible therapeutic formulations of the new compounds are, above all, tablets, dragees, capsules and suppositories, and also ampoules for parenteral (intravenous, subcutaneous and intramuscular) administration. The therapeutic unit dose is between 0.5 and 500 mg, preferably 10 to 100 mg, per tablet.

In addition to the customary fillers and excipients, these formulations can also contain an anti-hypertensive agent, especially for the treatment of high blood pressure, such as, for example, reserpine, hydralazine, quanethidine, α-methyldopa and clonidine, or a β-sympathicolytic active compound, such as, for example, propranolol.

Therapeutic combination formulations with potassium-retaining compounds, such as aldosterone antagonists, for example spironolactone or pseudoaldosterone antagonists, such as triamterene or amiloride, are also of interest. $K^+$ substitution in various use forms, for example dragees, tablets, effervescent tablets and elixirs, inter alia, is also possible.

Combinations of the compounds according to the invention with another agent having an anti-hyperuricaemic action, which in particular leads to an increase in anti-uricopathic effects by inhibition of xanthine oxidase, can also be of therapeutic interest.

In the examples which follow, the melting points and decomposition points of the embodiment examples are uncorrected.

In addition to the benzenesulfonamide derivatives described in the embodiment examples, it is also possible for the compounds of the general formula I or Ia summarized in the table which follows to be obtained according to the invention.

| $R^1$ | $R^2$ | $R^3$ | $R^4$ | $R^5$ | $R^6$ | $R^7$ | Y |
|---|---|---|---|---|---|---|---|
| $CH_3$ | H | H | H | H | H | $-C_2H_5$ | Cl |
| $CH_3$ | H | H | H | H | H | $-CH(CH_3)_2$ | Cl |
| $CH_3$ | H | H | H | H | H | $-C(CH_3)_3$ | Cl |
| $CH_3$ | H | H | H | H | H | $-(CH_2)_3CH_3$ | Cl |
| $CH_3$ | H | H | H | H | H | $-(CH_2)_3CH(CH_3)_2$ | Cl |
| $CH_3$ | H | H | H | H | H | $-(CH_2)_4CH_3$ | Cl |
| $CH_3$ | H | H | H | H | H | $CH_3CH-(CH_2)_2CH_3$ | Cl |
| $CH_3$ | H | H | H | H | H | $-CH(CH_2CH_3)_2$ | Cl |
| $CH_3$ | H | H | H | H | H | $-(CH_2)_6CH_3$ | Cl |
| $CH_3$ | H | H | H | H | H | $-(CH_2)_8CH_3$ | Cl |
| $CH_3$ | H | H | H | H | H | $-(CH_2)_9CH_3$ | Cl |
| $CH_3$ | H | H | H | H | H | $-(CH_2)_2-OCH_3$ | Cl |
| $CH_3$ | H | H | H | H | H | $-(CH_2)_3-OCH_3$ | Cl |
| $CH_3$ | H | H | H | H | H | $-CH_2-CH-CH_2$ with $OCH_3$, $OCH_3$ | Cl |
| $CH_3$ | H | H | H | H | H | $-CH_2-CH(OCH_3)_2$ | Cl |
| $CH_3$ | H | H | H | H | H | $-(CH_2)_2-CH(OCH_3)_2$ | Cl |
| $CH_3$ | H | H | H | H | H | $-(CH_2)_3-CH(OCH_3)_2$ | Cl |
| $CH_3$ | H | H | H | H | H | $-CH_2-CH$ (1,3-dioxolane) | Cl |
| $CH_3$ | H | H | H | H | H | $-(CH_2)_3-CH$ (1,3-dioxolane) | Cl |
| $CH_3$ | H | H | H | H | H | $-CH_2-C(OC_2H_5)_2$ with $CH_3$ | Cl |
| $CH_3$ | H | H | H | H | H | $-CH_2-C(CH_3)$ (1,3-dioxolane) | Cl |
| $CH_3$ | H | H | H | H | H | $H_3C-CH-C(OC_2H_5)_2$ with $CH_3$ | Cl |
| $CH_3$ | H | H | H | H | H | $H_3C-CH-C(CH_3)$ (1,3-dioxolane) | Cl |

-continued
| R¹ | R² | R³ | R⁴ | R⁵ | R⁶ | R⁷ | Y |
|---|---|---|---|---|---|---|---|
| CH₃ | H | H | H | H | H | (H₃C)₂CH—CH—C(OC₂H₅)₂<br>                                     CH₃ | Cl |
| CH₃ | H | H | H | H | H | 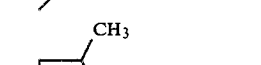 | Cl |
| CH₃ | H | H | H | H | H | 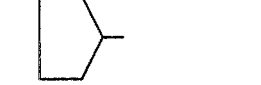 | Cl |
| CH₃ | H | H | H | H | H |  | Cl |
| CH₃ | H | H | H | H | H | 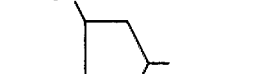 | Cl |
| CH₃ | H | H | H | H | H |  | Cl |
| CH₃ | H | H | H | H | H |  | Cl |
| CH₃ | H | H | H | H | H | 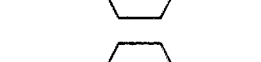 | Cl |
| CH₃ | H | H | H | H | H |  | Cl |
| CH₃ | H | H | H | H | H | 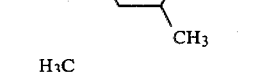 | Cl |
| CH₃ | H | H | H | H | H |  | Cl |
| CH₃ | H | H | H | H | H | 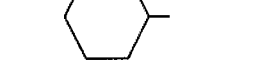 | Cl |
| CH₃ | H | H | H | H | H | 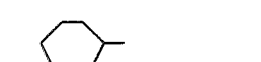 | Cl |
| CH₃ | H | H | H | H | H | 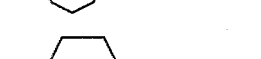 | Cl |
| CH₃ | H | H | H | H | H | 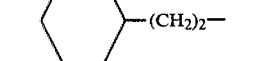 | Cl |

-continued

| R¹ | R² | R³ | R⁴ | R⁵ | R⁶ | R⁷ | Y |
|---|---|---|---|---|---|---|---|
| CH₃ | H | H | H | H | H | 3,4-(CH₃O)₂-C₆H₃-CH₂- | Cl |
| CH₃ | H | H | H | H | H | 2-CH₃-4-CH₃O-C₆H₃-CH₂- (4-OCH₃, 2-CH₃ on benzyl) | Cl |
| CH₃ | H | H | H | H | H | 4-CH₃-2-OCH₃-C₆H₃-CH₂- | Cl |
| CH₃ | H | H | H | H | H | 2,4-(CH₃)₂-C₆H₃-CH₂- (4-CH₃, 2-CH₃) | Cl |
| CH₃ | H | H | H | H | H | 2,5-(CH₃)₂-C₆H₃-CH₂- | Cl |
| CH₃ | H | H | H | H | H | 3-CH₃-C₆H₄-CH₂- | Cl |
| CH₃ | H | H | H | H | H | 2-CH₃-C₆H₄-CH₂- | Cl |
| CH₃ | H | H | H | H | H | 3-Cl-C₆H₄-CH₂- | Cl |
| CH₃ | H | H | H | H | H | 2,6-Cl₂-C₆H₃-CH₂- | Cl |
| CH₃ | H | H | H | H | H | 2,5-Cl₂-C₆H₃-CH₂- | Cl |
| CH₃ | H | H | H | H | H | 5-Cl-2-OCH₃-C₆H₃-CH₂- | Cl |
| CH₃ | H | H | H | H | H | 4-CH₃O-2-Cl-C₆H₃-CH₂- | Cl |

-continued

| R¹ | R² | R³ | R⁴ | R⁵ | R⁶ | R⁷ | Y |
|---|---|---|---|---|---|---|---|
| CH₃ | H | H | H | H | H | CH₃ | Br |
| CH₃ | H | H | H | H | H | (CH₂)₂CH₃ | Br |
| C₂H₅ | H | H | H | H | H | H | Br |
|  | H | H | H | H | H | H | Br |
| —CH₂—CH(O—CH₃)—CH₃ | H | H | H | H | H | H | Br |
| CH₂=CH—CH₂— | H | H | H | H | H | H | Br |
| CH₃ | H | H | H | H | H | —(CH₂)₃—CH₃ | Br |
| H | H | H | H | H | H | H | Br |
| CH₃ | H | H | H | H | H | —CH(CH₃)—CH₂—CH₃ | Br |
| CH₃ | H | H | H | H | H | —(CH₂)₅—CH₃ | Br |
| CH₃ | H | H | H | H | H | —(CH₂)₇—CH₃ | Br |
| CH₃ | H | H | H | H | H | —CH₂—CH=CH₂ | Br |
| CH₃ | H | H | H | H | H | —CH₂—CH(O—CH₃)—CH₃ | Br |
| CH₃ | H | H | H | H | H | —CH₂CH(OC₂H₅)₂ | Br |
| CH₃ | H | H | H | H | H |  | Br |
| CH₃ | H | H | H | H | H |  | Br |
| CH₃ | H | H | H | H | H | 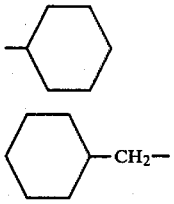 | Br |
| CH₃ | H | H | H | H | H | 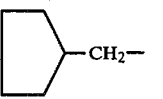 | Br |
| CH₃ | H | H | H | H | H | 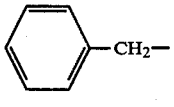 | Br |
| CH₃ | H | H | H | H | H | 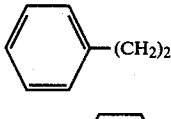 | Br |
| CH₃ | H | H | H | H | H | 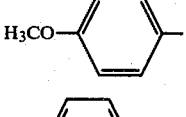 | Br |
| CH₃ | H | H | H | H | H | 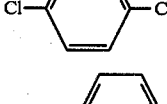 | Br |
| CH₃ | H | H | H | H | H | 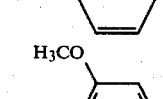 | Br |
| CH₃ | H | H | H | H | H | 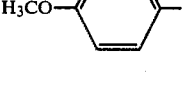 | Br |

-continued

| R¹ | R² | R³ | R⁴ | R⁵ | R⁶ | R⁷ | Y |
|---|---|---|---|---|---|---|---|
| CH₃ | H | H | H | H | H | 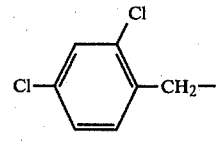 | Br |
| CH₃ | H | H | H | H | H |  | Br |
| CH₃ | H | H | H | H | C₂H₅ | C₂H₅ | Cl |
| CH₃ | H | H | H | H | —(CH₂)₃—CH₃ | —(CH₂)₃CH₃ | Cl |
| CH₃ | H | H | H | H | CH₃ | 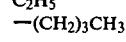 | Cl |
| CH₃ | H | H | H | H | CH₃ | —CH₂—CH(OCH₃)—CH₃ | Cl |
| CH₃ | H | H | H | H | CH₃ | 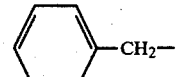 | Cl |
| CH₃ | H | H | H | H | CH₃ | —CH₂—CH=CH₂ | Cl |
| CH₃ | H | H | H | H | CH₃ | 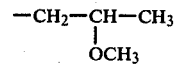 | Cl |
| CH₃ | H | H | H | H | CH₃ |  | Cl |
| CH₃ | H | H | H | H | CH₃ | 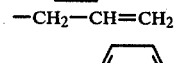 | Cl |
| CH₃ | H | H | H | H | CH₃ | —(CH₂)₃—CH₃ | Cl |
| CH₃ | H | H | H | H | CH₃ | —CH₂—CH(CH₃)₂ | Cl |
| CH₃ | H | H | H | H | CH₃ | CH₃ | Br |
| CH₃ | H | H | H | H | —(CH₂)₂—CH₃ | —(CH₂)₂CH₃ | Br |
| CH₃ | H | H | H | H | —(CH₂)₃—CH₃ | —(CH₂)₃CH₃ | Br |
| H | H | H | H | H | H | H | CF₃ |
| CH₃ | H | H | H | H | H | H | CF₃ |
| CH₃ | H | H | H | H | H | CH₃ | CF₃ |
| CH₃ | H | H | H | H | H | —(CH₂)₃CH₃ | CF₃ |
| CH₃ | H | H | H | H | H | CH₃—CH—CH₂CH₃ | CF₃ |
| CH₃ | H | H | H | H | CH₃ | CH₃ | CF₃ |
| CH₃ | H | H | H | H | —(CH₂)₂—CH₃ | —(CH₂)₂—CH₃ | CF₃ |
| CH₃ | H | H | H | H | H | —(CH₂)₅—CH₃ | CF₃ |
| CH₃ | H | H | H | H | H | CH₂—CH=CH₂ | CF₃ |
| CH₃ | H | H | H | H | H |  | CF₃ |
| CH₃ | H | H | H | H | H | —CH₂—CH(OC₂H₅)₂ | CF₃ |
|  | H | H | H | H | H | H | CF₃ |

-continued

| R¹ | R² | R³ | R⁴ | R⁵ | R⁶ | R⁷ | Y |
|---|---|---|---|---|---|---|---|
| CH$_2$—CH—CH$_3$ \| OCH$_3$ | H | H | H | H | H | H | CF$_3$ |
| H | H | H | H | H | H | H | H |
| CH$_3$ | H | H | H | H | H | H | H |
| CH$_3$ | H | H | H | H | H | CH$_3$ | H |
| CH$_3$ | H | H | H | H | H | CH$_2$CH$_3$ | H |
| CH$_3$ | H | H | H | H | H | (CH$_2$)$_2$CH$_3$ | H |
| CH$_3$ | H | H | H | H | H | (CH$_2$)$_3$CH$_3$ | H |
| CH$_3$ | H | H | H | H | H | CH$_3$—CH—CH$_2$CH$_3$ | H |
| CH$_3$ | H | H | H | H | H | —(CH$_2$)$_5$CH$_3$ | H |
| CH$_3$ | H | H | H | H | H | 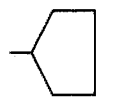 | H |
| CH$_3$ | H | H | H | H | H | 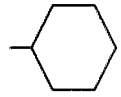 | H |
| CH$_3$ | H | H | H | H | H | —CH$_2$—<cyclohexyl> | H |
| CH$_3$ | H | H | H | H | H | —CH$_2$—<phenyl> | H |
| CH$_3$ | H | H | H | H | H | —CH$_2$—<phenyl>—OCH$_3$ | H |
| H | H | H | H | H | H | H | CH$_3$ |
| CH$_3$ | H | H | H | H | H | H | CH$_3$ |
| CH$_3$ | H | H | H | H | H | CH$_3$ | CH$_3$ |
| CH$_3$ | H | H | H | H | H | C$_2$H$_5$ | CH$_3$ |
| CH$_3$ | H | H | H | H | H | —(CH$_2$)$_2$CH$_3$ | CH$_3$ |
| CH$_3$ | H | H | H | H | H | —(CH$_2$)$_3$CH$_3$ | CH$_3$ |
| CH$_3$ | H | H | H | H | H | H$_3$C—CH—CH$_2$—CH$_3$ | CH$_3$ |
| CH$_3$ | H | H | H | H | H | —(CH$_2$)$_5$—CH$_3$ | CH$_3$ |
| CH$_3$ | H | H | H | H | H | <cyclopentyl> | CH$_3$ |
| CH$_3$ | H | H | H | H | H | <cyclohexyl> | CH$_3$ |
| CH$_3$ | H | H | H | H | H | —CH$_2$—<cyclohexyl> | CH$_3$ |
| CH$_3$ | H | H | H | H | H | —CH$_2$—CH(OC$_2$H$_5$)$_2$ | CH$_3$ |
| CH$_3$ | H | H | H | H | H | —CH$_2$—<phenyl> | CH$_3$ |
| CH$_3$ | H | H | H | H | H | CH$_3$O—<phenyl>—CH$_2$— | CH$_3$ |
| H | CH$_3$ | H | H | H | H | H | Cl |
| CH$_3$ | CH$_3$ | H | H | H | H | H | Cl |
| CH$_3$ | CH$_3$ | H | H | H | H | CH$_3$ | Cl |
| CH$_3$ | CH$_3$ | H | H | H | H | —(CH$_2$)$_2$CH$_3$ | Cl |
| CH$_3$ | CH$_3$ | H | H | H | H | —(CH$_2$)$_3$CH$_3$ | Cl |

-continued

| R¹ | R² | R³ | R⁴ | R⁵ | R⁶ | R⁷ | Y |
|---|---|---|---|---|---|---|---|
| CH₃ | CH₃ | H | H | H | H | CH₃—CH—CH₂CH₃ | Cl |
| CH₃ | CH₃ | H | H | H | H | —(CH₂)₅CH₃ | Cl |
| CH₃ | CH₃ | H | H | H | H |  | Cl |
| CH₃ | CH₃ | H | H | H | H | —CH₂CH(OC₂H₅)₂ | Cl |
| CH₃ | CH₃ | H | H | H | H | 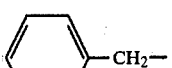 | Cl |
| CH₃ | CH₃ | H | H | H | CH₃ | CH₃ | Cl |
| CH₃ | CH₃ | H | H | H | (CH₂)₂—CH₃ | —(CH₂)₂—CH₃ | Cl |
| H | H | H | CH₃ | H | H | H | Cl |
| CH₃ | H | H | CH₃ | H | H | H | Cl |
| CH₃ | H | H | CH₃ | H | H | CH₃ | Cl |
| CH₃ | H | H | CH₃ | H | H | —(CH₂)₂CH₃ | Cl |
| C₂H₅ | H | H | CH₃ | H | H | H | Cl |
| CH₃ | H | H | CH₃ | H | H | CH₃CH—CH₂CH₃ | Cl |
| CH₃ | H | H | CH₃ | H | H | —(CH₂)₅CH₃ | Cl |
| CH₃ | H | H | CH₃ | H | H | —(CH₂)₇CH₃ | Cl |
| CH₃ | H | H | CH₃ | H | H |  | Cl |
| CH₃ | H | H | CH₃ | H | H |  | Cl |
| CH₃ | H | H | CH₃ | H | H |  | Cl |
| CH₃ | H | H | CH₃ | H | H |  | Cl |
| CH₃ | H | H | CH₃ | H | H | —CH₂—CH—CH₃ with OCH₃ | Cl |
| CH₃ | H | H | CH₃ | H | H | —CH₂(OC₂H₅)₂ | Cl |
| CH₃ | H | H | CH₃ | H | H | —(CH₂)₃CH₃ | Cl |
| CH₃ | H | H | CH₃ | H | H | 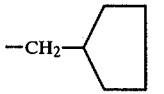 | Cl |
| CH₃ | H | H | CH₃ | H | H | 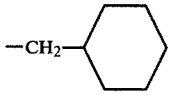 | Cl |
| CH₃ | H | H | CH₃ | H | H | 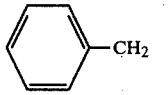 | Cl |
| CH₃ | H | H | CH₃ | H | H | 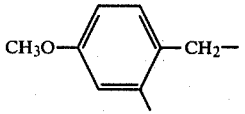 | Cl |
| CH₃ | H | H | CH₃ | H | H | 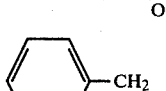 | Cl |

-continued

| R¹ | R² | R³ | R⁴ | R⁵ | R⁶ | R⁷ | Y |
|---|---|---|---|---|---|---|---|
| CH₃ | H | H | CH₃ | H | H | H₃C—C₆H₄—CH₂— | Cl |
| H | H | H | CH₃ | H | H | H | Br |
| CH₃ | H | H | CH₃ | H | H | CH₃ | Br |
| CH₃ | H | H | CH₃ | H | H | —(CH₂)₃CH₃ | Br |
| CH₃ | H | H | CH₃ | H | CH₃ | CH₃ | Cl |
| CH₃ | H | H | CH₃ | H | —(CH₂)₂CH₃ | —(CH₂)₂CH₃ | Cl |
| H | CH₃ | H | CH₃ | H | H | H | Cl |
| CH₃ | CH₃ | H | CH₃ | H | H | H | Cl |
| CH₃ | CH₃ | H | CH₃ | H | H | H | Br |
| CH₃ | CH₃ | H | CH₃ | H | H | CH₃ | Cl |
| CH₂—CH=CH₂ | CH₃ | H | CH₃ | H | H | H | Cl |
| CH₃ | CH₃ | H | CH₃ | H | CH₃ | CH₃ | Cl |
| CH₃ | CH₃ | H | CH₃ | H | H | CH₃—CH—CH₂—CH₃ | Cl |
| CH₃ | CH₃ | H | CH₃ | H | H | —(CH₂)₃CH₃ | Cl |
| H | H | H | CH₃ | CH₃ | H | H | Cl |
| CH₃ | H | H | CH₃ | CH₃ | H | H | Cl |
| —C₂H₅ | H | H | CH₃ | CH₃ | H | H | Cl |
| —CH(CH₃)₂ | H | H | CH₃ | CH₃ | H | H | Cl |
| —CH₂—CH=CH₂ | H | H | CH₃ | CH₃ | H | H | Cl |
| cyclopropyl | H | H | CH₃ | CH₃ | H | H | Cl |
| CH₃ | H | H | CH₃ | CH₃ | H | CH₃ | Cl |
| CH₃ | H | H | CH₃ | CH₃ | H | (CH₂)₃CH₃ | Cl |
| CH₃ | H | H | CH₃ | CH₃ | CH₃ | CH₃ | Cl |
| CH₃ | H | H | CH₃ | CH₃ | —(CH₂)₂CH₃ | —(CH₂)₂CH₃ | Cl |
| CH₃ | H | H | CH₃ | CH₃ | H | —CH₂—C₆H₅ | Cl |
| CH₃ | H | H | CH₃ | CH₃ | H | H | Br |
| CH₃ | H | H | CH₃ | CH₃ | H | H | H |
| CH₃ | H | H | CH₃ | CH₃ | H | cyclopentyl | Cl |
| H | CH₃ | CH₃ | H | H | H | H | Cl |
| CH₃ | CH₃ | CH₃ | H | H | H | H | Cl |
| C₂H₅ | CH₃ | CH₃ | H | H | H | H | Cl |
| H | CH₃ | CH₃ | H | H | H | H | Cl |
| CH₃ | CH₃ | CH₃ | H | H | H | CH₃ | Cl |
| CH₃ | CH₃ | CH₃ | H | H | H | —(CH₂)₃CH₃ | Cl |
| CH₃ | CH₃ | CH₃ | H | H | H | —(CH₂)₅CH₃ | Cl |
| CH₃ | CH₃ | CH₃ | H | H | H | cyclopentyl | Cl |
| CH₃ | CH₃ | CH₃ | H | H | H | —CH₂—C₆H₅ | Cl |
| CH₃ | CH₃ | CH₃ | H | H | CH₃ | CH₃ | Cl |
| CH₃ | CH₃ | CH₃ | H | H | —(CH₂)₂CH₃ | —(CH₂)₂CH₃ | Cl |
| CH₃ | H | H | C₂H₅ | H | H | H | Cl |
| CH₃ | H | H | C₂H₅ | H | H | CH₃ | Cl |
| CH₃ | H | H | C₂H₅ | H | H | —(CH₂)₂CH₃ | Cl |
| CH₃ | H | H | C₂H₅ | H | H | —(CH₂)₅CH₃ | Cl |
| CH₃ | H | H | C₂H₅ | H | —(CH₂)₂CH₃ | —(CH₂)₂CH₃ | Cl |
| CH₃ | C₂H₅ | H | H | H | H | H | Cl |
| CH₃ | C₂H₅ | H | H | H | H | CH₃ | Cl |
| CH₃ | C₂H₅ | H | H | H | H | —(CH₂)₃CH₃ | Cl |
| CH₃ | C₂H₅ | H | H | H | H | —CH₂—C₆H₅ | Cl |
| CH₃ | C₂H₅ | H | H | H | —(CH₂)₂CH₃ | —(CH₂)₂CH₃ | Cl |
| CH₃ | C₂H₅ | C₂H₅ | H | H | H | H | Cl |
| CH₃ | H | H | —(CH₂)₂CH₃ | H | H | H | Cl |
| CH₃ | H | H | —CH(CH₃)₂ | H | H | H | Cl |

-continued

| R¹ | R² | R³ | R⁴ | R⁵ | R⁶ | R⁷ | Y |
|---|---|---|---|---|---|---|---|
| CH₃ | H | H | —(CH₂)₃CH₃ | H | H | H | Cl |
| CH₃ | H | H | —(CH₂)₃CH₃ | H | H | CH₃ | Cl |
| CH₃ | H | H | —(CH₂)₃CH₃ | H | H | —(CH₂)₃CH₃ | Cl |
| CH₃ | H | H | H | H | CH₃ | CH₃ | Cl |
| CH₃ | —(CH₂)₂CH₃ | H | H | H | H | H | Cl |
| CH₃ | —(CH₂)₂CH₃ | H | H | H | H | CH₃ | Cl |
| CH₃ | —(CH₂)₂CH₃ | H | H | H | H | —(CH₂)₃CH₃ | Cl |
| CH₃ | —(CH₂)₃CH₃ | H | H | H | H | H | Cl |
| CH₃ | —(CH₂)₃CH₃ | H | H | H | H | CH₃ | Cl |
| CH₃ | —(CH₂)₃CH₃ | H | H | H | CH₃ | CH₃ | Cl |
| CH₃ | —(CH₂)₃CH₃ | H | CH₃ | H | H | H | Cl |
| CH₃ | —CH(CH₃)₂ | H | H | H | H | H | Cl |
| CH₃ | —CH(CH₃)₂ | H | H | H | H | CH₃ | Cl |
| CH₃ | —CH(CH₃)₂ | H | H | H | H | (CH₂)₃CH₃ | Cl |
| CH₃ | —CH₂—CH(CH₃)₂ | H | H | H | H | CH₃ | Cl |
| CH₃ | —CH₂CH(CH₃)₂ | H | H | H | H | H | Cl |
| CH₃ | —CH₂CH(CH₃)₂ | H | H | H | CH₃ | CH₃ | Cl |
| CH₃ | C₂H₅ | C₂H₅ | H | H | H | H | Cl |
| CH₃ | C₂H₅ | C₂H₅ | H | H | H | CH₃ | Cl |
| CH₃ | C₂H₅ | C₂H₅ | H | H | H | —(CH₂)₃CH₃ | Cl |
| CH₃ | C₂H₅ | C₂H₅ | H | H | CH₃ | CH₃ | Cl |
| CH₃ | CH₃ | CH₃ | CH₃ | H | H | H | Cl |
| CH₃ | CH₃ | CH₃ | CH₃ | H | H | CH₃ | Cl |
| CH₃ | CH₃ | CH₃ | CH₃ | H | CH₃ | CH₃ | Cl |
| CH₃ | CH₃ | H | CH₃ | CH₃ | H | H | Cl |
| CH₃ | CH₃ | H | CH₃ | CH₃ | H | CH₃ | Cl |
| CH₃ | CH₃ | H | CH₃ | CH₃ | CH₃ | CH₃ | Cl |
| CH₃ | CH₃ | CH₃ | CH₃ | H | (CH₂)₂CH₃ | (CH₂)₂CH₃ | Cl |
| CH₃ | CH₃ | CH₃ | CH₃ | CH₃ | H | H | Cl |
| CH₃ | CH₃ | CH₃ | CH₃ | CH₃ | H | CH₃ | Cl |
| CH₃ | CH₃ | CH₃ | CH₃ | CH₃ | H | (CH₂)₂CH₃ | Cl |
| CH₃ | CH₃ | CH₃ | CH₃ | CH₃ | H | (CH₂)₅CH₃ | Cl |
| CH₃ | CH₃ | CH₃ | CH₃ | CH₃ | CH₃ | CH₃ | Cl |
| CH₃ | CH₃ | CH₃ | CH₃ | CH₃ | (CH₂)₂CH₃ | (CH₂)₂CH₃ | Cl |

EXAMPLE 1

5-(4-Chloro-3-sulfamoylphenyl)-5-hydroxy-1-methyl-2-oxopyrrolidine or 4-(4-chloro-3-sulfamoylphenyl)-4-oxo-butanoic acid methylamide (Method I)

7.3 g of 4-(4-chloro-3-sulfamoylphenyl)-4-oxobutanoic acid are suspended in 50 ml of absolute tetrahydrofuran and, after adding 3.8 ml of triethylamine, the mixture is cooled to −5° C. and 2.6 ml of ethyl chloroformate are then added. The mixture is stirred at 0° for about 5 to 10 minutes, 30 ml of aqueous methylamine solution (40% strength) are added and the reaction mixture is allowed to come slowly to room temperature. It is concentrated to about half the volume under reduced pressure and adjusted to pH 6-7 with 2 N HCl, whilst cooling, and the amorphous precipitate is caused to crystallize. Colorless crystals, melting point 147°-149° C.

EXAMPLE 2

5-(4-Chloro-3-sulfamoylphenyl)-5-hydroxy-1-methyl-2-oxopyrrolidine or 4-(4-chloro-3-sulfamoylphenyl)-4-oxo-butanoic acid methylamide (Method II)

(a) 27 g of 4-(4-chloro-3-sulfamoylphenyl)-4-oxobutanoic acid are dissolved in 200 ml of methanol, 1 g of acetyl chloride is added and the mixture is stirred at room temperature. After 24 hours, only small amounts of starting material can still be detected in the thin layer chromatogram. The solvent is driven off, the residue is treated with 200 ml of acetic acid/200 ml of water and, after the pH has been adjusted to 8 with saturated sodium bicarbonate solution, the mixture is stirred vigorously for 30 minutes. After separating off the organic phase and drying it over sodium sulfate, the solvent is distilled off and methyl 4-(4-chloro-3-sulfamoylphenyl)-4-oxobutanoate is obtained.

Colorless crystals, melting point 113°-115° C.

Analogously, for example, 4-(4-chloro-3-sulfamoylphenyl)-4-oxobutanoic acid and acetyl chloride in (α) ethanol give ethyl 4-(4-chloro-3-sulfamoylphenyl)-4-oxobutanoate (melting point 94°-95° C.), and (β) isopropanol give isopropyl 4-(4-chloro-3-sulfamoylphenyl)-4-oxobutanoate (melting point 128°-130° C.).

(b) 8 g of methyl 4-(4-chloro-3-sulfamoylphenyl)-4-oxobutanoate are introduced into a solution of 6 g of gaseous methylamine in 80 ml of methanol, whilst stirring, and the mixture is left to stand at room temperature. The progress of the reaction is followed on a thin layer chromatogram (silica gel, ethyl acetate). When the starting material can no longer be detected (about 48 hours), the solvent is driven off under reduced pressure, water is added to the residue, the pH is adjusted to 6 to 5 with 2 N HCl and the amorphous precipitate is kneaded thoroughly, under the aqueous phase. After leaving the mixture to stand overnight, the crystals are filtered off. Melting point 145°-148° C.

Analogously, 5-(4-chloro-3-sulfamoylphenyl)-5-hydroxy-1-methyl-2-oxopyrrolidine is also obtained, for example, by reacting methylamine with ethyl 4-(4-chloro-3-sulfamoylphenyl)-4-oxo-butanoate or with isopropyl 4-(4-chloro-3-sulfamoylphenyl)-4-oxobutanoate.

EXAMPLE 3

4-(4-Chloro-3-sulfamoylphenyl)-4-oxobutanoic acid ethylamide or
1-ethyl-5-(4-chloro-3-sulfamoylphenyl)-5-hydroxy-2-oxopyrrolidine is obtained analogously to the instructions indicated in Example (2b) by reacting 6 g of methyl 4-(4-chloro-3-sulfamoylphenyl)-4-oxobutanoate with a solution of 9 g of ethylamine in 90 ml of methanol.

Colorless crystals, melting point 164°–166° C., decomposition from 182° C.

EXAMPLE 4

4-(Chloro-3-sulfamoylphenyl)-4-oxobutanoic acid amide or
5-(4-chloro-3-sulfamoylphenyl)-5-hydroxy-2-oxopyrrolidine is obtained analogously to the instructions indicated in Example 1 using 100 ml of aqueous ammonia (25% strength) instead of the methylamine solution.

Colorless crystals, decomposition from 173° C.

EXAMPLE 5

4-(4-Chloro-3-sulfamoylphenyl)-4-oxobutanoic acid isopropylamide or
5-(4-chloro-3-sulfamoylphenyl)-5-hydroxy-1-isopropyl-2-oxo-pyrrolidine is obtained analogously to the instructions indicated in Example 1 using a solution of 1.7 g of isopropylamine (instead of methylamine) in 20 ml of tetrahydrofuran. The reaction mixture is stirred at room temperature for 20 hours, the solvent is driven off, 100 ml of water are added and the mixture is extracted with 100 ml of ethyl acetate. After drying the extract over sodium sulfate, the solvent is distilled off under reduced pressure, the residue is stirred under diisopropyl ether for 2 hours and the colorless crystals are filtered off. Melting point 164° C.

EXAMPLE 6

4-(4-Chloro-3-sulfamoylphenyl)-4-oxobutanoic acid isobutylamide or
5-(4-chloro-3-sulfamoylphenyl)-5-hydroxy-1-isobutyl-2-oxopyrrolidine is obtained analogously to the instructions indicated in Example 1 using a solution of 2.2 g of isobutylamine (instead of methylamine) in 20 ml of tetrahydrofuran. The mixture is worked up analogously to the instructions indicated in Example 5.

Colorless crystals, melting point 129° C. (from chloroform).

EXAMPLE 7

4-(4-Chloro-3-sulfamoylphenyl)-4-oxobutanoic acid 2-methoxypropylamide or
5-(4-chloro-3-sulfamoylphenyl)-5-hydroxy-1-(2-methoxypropyl)-2-oxopyrrolidine is obtained analogously to the instructions indicated in Example 1 using a solution of 2.6 g of 2-methoxypropylamine (instead of methylamine) in 20 ml of tetrahydrofuran. The mixture is worked up analogously to the instructions indicated in Example 5.

Colorless crystals from isopropanol, melting point 127° C.

EXAMPLE 8

4-(4-Chloro-3-sulfamoylphenyl)-4-oxobutanoic acid allylamide or
1-allyl-5-(4-chloro-3-sulfamoylphenyl)-5-hydroxy-2-oxopyrrolidine is obtained analogously to the instructions indicated in Example 1 using a solution of 1.6 g of allylamine (instead of methylamine) in 20 ml of tetrahydrofuran, and the mixture is worked up analogously to the instructions indicated in Example 5.

Colorless amorphous solid, melting point 86° C., with decomposition.

EXAMPLE 9

4-(4-Chloro-3-sulfamoylphenyl)-4-oxobutanoic acid cyclopropylamide or
5-(4-chloro-3-sulfamoylphenyl)-1-cyclopropyl-5-hydroxy-2-oxopyrrolidine is obtained analogously to the instructions indicated in Example 2(b) from 6 g of methyl 4-(4-chloro-3-sulfamoylphenyl)-4-oxobutanoate and 6 g of cyclopropylamine, the mixture being left to stand at room temperature for 3 weeks.

Colorless crystals, decomposition point 128° C.

EXAMPLE 10

4-(4-Chloro-3-sulfamoylphenyl)-4-oxobutanoic acid cyclopentylamide or
5-(4-chloro-3-sulfamoylphenyl)-1-cyclopentyl-5-hydroxy-2-oxopyrrolidine is obtained analogously to the instructions indicated in Example 2(b) from 6 g of methyl 4-(4-chloro-3-sulfamoylphenyl)-4-oxobutanoate and 6 g of cyclopentylamine, the reaction time being about 2 weeks at room temperature.

Colorless crystals, melting point 153° C. (decomposition).

EXAMPLE 11

5-(4-Bromo-3-sulfamoylphenyl)-5-hydroxy-1-methyl-2-oxopyrrolidine or
4-(4-bromo-3-sulfamoylphenyl)-4-oxobutanoic acid methylamide (a) 10 g of 4-(4-bromophenyl)-4-oxobutanoic acid are introduced into 100 ml of nitric acid ($\delta = 1.52$) at $-15°$ C. and the reaction mixture is subsequently stirred at $-10°$ C. for 1½ hours and then poured onto ice, whilst stirring. The crystalline 4-(4-bromo-3-nitrophenyl)-4-oxobutanoic acid is filtered off and rinsed with water.

Colorless to pale yellow crystals, melting point 165° C.

(b) 3.6 ml of concentrated HCl are added dropwise to a mixture of 10 g of 4-(4-bromo-3-nitrophenyl)-4-oxobutanoic acid and 6.5 g of iron powder, the mixture is then boiled under a reflux condenser for 4 hours and undissolved material is filtered off hot. The filtrate is evaporated and, after adding water and 5 ml of 2 N HCl, the oily residue is extracted with ethyl acetate and, after drying the organic phase over sodium sulfate, the solvent is distilled off. Colorless crystalline 4-(3-amino-4-bromophenyl)-4-oxobutanoic acid is obtained, melting point 169°–171° (from water/glacial acetic acid).

(c) A solution of 1.3 g of sodium nitrite in 10 ml of water is added dropwise to a suspension of 5 g of 4-(3-amino-4-bromophenyl)-4-oxobutanoic acid in 50 ml of 20% strength hydrochloric acid at 0° to −5° C. The reaction mixture is poured into a suspension of 3.1 g of CuCl$_2$.2H$_2$O in 100 ml of glacial acetic acid solution saturated with SO$_2$, and the mixture is stirred for about 30 minutes and then diluted with the same volume of water. Colorless crystalline 4-(4-bromo-3-chlorosulfonylphenyl)-4-oxobutanoic acid of melting point 183°–185° C. is obtained.

(d) 4 g of 4-(4-bromo-3-chloro-sulfonylphenyl)-4-oxobutanoic acid are introduced into 70 ml of aqueous ammonia solution (25% strength) and the mixture is stirred at room temperature for 6 hours. About ¼ of the volume is distilled off, the mixture is adjusted to pH 1 to 0 with hydrochloric acid and the crystalline 4-(4-bromo-3-sulfamoylphenyl)-4-oxobutanoic acid is filtered off, melting point 176°–178° C. (from water).

(e) 1.5 g of 4-(4-bromo-3-sulfamoylphenyl)-4-oxobutanoic acid are converted, in a mixture of 0.2 g of acetyl chloride in 30 ml of methanol, analogously to the instructions indicated in Example 2(a), into methyl 4-(4-bromo-3-sulfamoylphenyl)-4-oxobutanoate, melting point 110°–112° C.

(f) 5-(4-Bromo-3-sulfamoylphenyl)-5-hydroxy-1-methyl-2-oxopyrrolidine is obtained analogously to the instructions indicated in Example 2(b) from 8 g of methyl 4-(4-bromo-3-sulfamoylphenyl)-4-oxobutanoate and 8 g of methylamine.

Colorless crystals, melting point 148° C.

EXAMPLE 12

4-(4-Chloro--sulfamoylphenyl)-4-oxobutanoic acid benzylamide or
1-benzyl-5-(4-chloro-3-sulfamoylphenyl)-5-hydroxy-2-oxopyrrolidine is obtained analogously to the instructions indicated in Example 1 using a solution of 3.2 g of benzylamine (instead of methylamine) in 20 ml of tetrahydrofuran. The mixture is worked up analogously to the instructions indicated in Example 5.

Colorless crystals, melting point 114°–116° C.

EXAMPLE 13

5-(4-Chloro-3-sulfamoylphenyl)-5-hydroxy-1-methyl-2-oxopyrrolidine or
4-(4-chloro-3-sulfamoylphenyl)-4-oxobutanoic acid methylamide is obtained analogously to the instructions indicated in Example 1 using 3.1 g of methanesulfonyl chloride instead of ethyl chloroformate.

Colorless crystals. Melting point 146°–148° C. The mixed melting point with the product from Example 1 showed no depression.

EXAMPLE 14

5-(4-Chloro-3-sulfamoylphenyl)-5-hydroxy-1-methyl-2-oxopyrrolidine or
4-(4-chloro-3-sulfamoylphenyl)-4-oxobutanoic acid methylamide (a) 3.8 g of sodium boranate are added in portions to a mixture of 7.3 g of 4-(4-chloro-3-sulfamoylphenyl)-4-oxobutanoic acid, 100 ml of ethanol and 2.5 g of triethylamine at 10° C., whilst stirring, the mixture is stirred at room temperature for a further 2.5 hours and the solvent is driven off. The residue is taken up in a little water and the solution is rendered acid with HCl (concentrated). After standing for 2 days, the crystalline 5-(4-chloro-3-sulfamoylphenyl)-butyrolactone is filtered off. Melting point 156°–157° C. (from diisopropyl ether).

(b) 2.4 g of 5-(4-chloro-3-sulfamoylphenyl)-butyrolactone are stirred in 60 ml of methanol with 1 g of methylamine at room temperature for 15 hours, the mixture is then heated to 100° C. in an autoclave for 1 hour and the solvent is distilled off under reduced pressure. The oily residue, consisting of 4-(4-chloro-3-sulfamoylphenyl)-4-hydroxybutanoic acid methylamide, is dissolved in 100 ml of acetonitrile and, after adding 20 g of active manganese-IV oxide, the mixture is stirred at room temperature for 3 hours and filtered. The inorganic residue is washed once with acetone and the combined filtrate phases are concentrated.

Colorless crystals, melting point 146°–148° C.

EXAMPLE 15

5-(4-Chloro-3-methylsulfamoylphenyl)-5-hydroxy-1-methyl-2-oxopyrrolidine or
4-(4-chloro-3-methylsulfamoyl)-4-oxobutanoic acid methylamide (a) 15.5 g of 4-(4-chloro-3-chlorosulfamoylphenyl)-4-oxobutanoic acid are introduced in portions into a solution of 10 g of gaseous methylamine in 100 ml of methanol, whilst cooling with ice and stirring, and the mixture is stirred at room temperature for 18 hours. The solvent is driven off, 300 ml of water are added to the residue, the mixture is rendered acid with concentrated HCl and the crystalline 4-(4-chloro-3-methylsulfamoylphenyl)-4-oxobutanoic acid of melting point 144° C. is filtered off.

(b) A mixture of 12 g of 4-(4-chloro-3-methylsulfamoylphenyl)-4-oxobutanoic acid and 1.2 g of acetyl chloride in 120 ml of methanol is reacted for 48 hours and worked up, analogously to the instructions indicated in Example 2(a). Methyl 4-(4-chloro-3-methylsulfamoylphenyl)-4-oxobutanoate of melting point 112°–114° C. (from ethanol) is obtained.

(c) 7.9 of methyl 4-(4-chloro-3-methylsulfamoylphenyl)-4-oxobutanoate are reacted with 6.9 g of methylamine in 100 ml of methanol and the mixture is worked up analogously to the instructions indicated in Example 2(b). 5-(4-Chloro-3-methylsulfamoylphenyl)-5-hydroxy-1-methyl-2-oxopyrrolidine of melting point 147°–150° C. is obtained.

EXAMPLE 16

5-(4-Chloro-3-propylsulfamoylphenyl)-5-hydroxy-1-methyl-2-oxopyrrolidine or
4-(4-chloro-3-propylsulfamoylphenyl)-4-oxobutanoic acid methylamide (a) 4-(4-Chloro-3-propylsulfamoylphenyl)-4-oxobutanoic acid is obtained analogously to the instructions indicated in Example 15(a) using 9 g of n-propylamine instead of the methylamine. Colorless crystals, melting point 106° C.

(b) Methyl 4-(4-chloro-3-propylsulfamoylphenyl)-4-oxobutanoate is obtained analogously to the instructions indicated in Example 2(a). Melting point 93°–94° C.

(c) 5-(4-Chloro-3-propylsulfamoylphenyl)-5-hydroxy-1-methyl-2-oxopyrrolidine is obtained analogously to the instructions indicated in Example 2(b) from 10.1 g of methyl 4-(4-chloro-3-propylsulfamoylphenyl)-4-oxobutanoate and 7 g of methylamine.

Melting point 167°–169° C.

EXAMPLE 17

4-(4-Chloro-3-methylsulfamoylphenyl)-4-oxobutanoic acid amide or
5-(4-chloro-3-methylsulfamoylphenyl)-5-hydroxy-2-oxopyrrolidine is obtained analogously to the instructions indicated in Example 1 using 7.5 g of 4-(4-chloro-3-methylsulfamoylphenyl)-4-oxobutanoic acid, 3.8 ml of triethylamine, 2.6 ml of ethyl chloroformate and 150 ml of 25% strength aqueous ammonia solution in tetrahydrofuran as the solvent.

Melting point 108°–110° C.

EXAMPLE 18

5-(4-Chloro-3-sec.-butylsulfamoylphenyl)-5-hydroxy-1-methyl-2-oxopyrrolidine or
4-(4-chloro-3-sec.-butylsulfamoylphenyl)-4-oxobutanoic acid methylamide (a) 4-(4-Chloro-3-sec.-butylsulfamoylphenyl)-4-oxobutanoic acid is obtained analogously to the instructions indicated in Example 15(a) using 13 g of sec.-butylamine instead of methylamine.

Melting point 133°.

(b) 5-(4-Chloro-3-sec.-butylsulfamoylphenyl)-5-hydroxy-1-methyl-2-oxopyrrolidine is obtained analogously to the instructions indicated in Example 1 using 4.2 g of 4-(4-chloro-3-sec.-butylsulfamoylphenyl)-4-oxobutanoic acid, 1.7 ml of triethylamine, 1.2 ml of ethyl chloroformate and 20 ml of 40% strength aqueous methylamine solution in tetrahydrofuran as the solvent.

Colorless crystals of melting point 138° C.

EXAMPLE 19

5-(4-Chloro-3-n-hexylsulfamoylphenyl)-5-hydroxy-1-methyl-2-oxopyrrolidine is obtained analogously to the instructions indicated in Example 1 from 7.5 g of 4-(4-chloro-3-n-hexylsulfamoylphenyl)-4-oxobutanoic acid and 100 ml of 40% strength aqueous methylamine solution using 3.2 g of triethylamine and 2.2 ml of ethyl chloroformate.

Colorless crystals, melting point 114°–117° C.

The 4-(4-chloro-3-n-hexylsulfamoylphenyl)-4-oxobutanoic acid required is obtained analogously to the instructions indicated in Example 15(a) using 7.5 g of n-hexylamine.

Colorless crystals, melting point 115°–118° C.

EXAMPLE 20

5-(4-Chloro-3-isobutylsulfamoylphenyl)-5-hydroxy-1-methyl-2-oxopyrrolidine (a) 4-(4-Chloro-3-isobutylsulfamoylphenyl)-4-oxobutanoic acid is obtained analogously to the instructions indicated in Example 15(a) from 8 g of isobutylamine and 9.3 g of 4-(4-chloro-3-chlorosulfonylphenyl)-4-oxobutanoic acid.

Colorless crystals, melting point 128°–130° C.

(b) 5-(4-Chloro-3-isobutylsulfamoylphenyl)-5-hydroxy-1-methyl-2-oxopyrrolidine is obtained analogously to the instructions indicated in Example 1 from 4-(4-chloro-3-isobutylsulfamoylphenyl)-4-oxo-butanoic acid and 100 ml of 40% strength aqueous methylamine solution using 3.2 ml of triethylamine and 2.2 ml of ethyl chloroformate.

Colorless crystals, melting point 144°–147° C.

EXAMPLE 21

5-(3-Allylsulfamoyl-4-chlorophenyl)-5-hydroxy-1-methyl-2-oxopyrrolidine (a) 4-(3-Allylsulfamoyl-4-chlorophenyl)-4-oxobutanoic acid is obtained analogously to the instructions indicated in Example 15(a) from 9.3 g of 4-(4-chloro-3-chlorosulfonylphenyl)-4-oxobutanoic acid and 6 g of allylamine.

Colorless crystals, melting point 107°–109° C.

(b) 5-(3-Allylsulfamoyl-4-chlorophenyl)-5-hydroxy-1-methyl-2-oxopyrrolidine is obtained analogously to the instructions indicated in Example 1 from 6.6 g of 4-(3-allylsulfamoyl-4-chlorophenyl)-4-oxobutanoic acid and 100 ml of 40% strength aqueous methylamine solution using 3.2 g of triethylamine and 2.2 ml of ethyl chloroformate.

Colorless crystals, melting point 133°–135° C.

EXAMPLE 22

5-(4-Chloro-3-cyclopentylsulfamoylphenyl)-5-hydroxy-1-methyl-2-oxopyrrolidine (a) 4-(4-Chloro-3-cyclopentylsulfamoylphenyl)-4-oxobutanoic acid is obtained analogously to the instructions indicated in Example 15(a) from 10 g of 4-(4-chloro-3-chlorosulfonylphenyl)-4-oxobutanoic acid and 10.9 g of cyclopentylamine.

Colorless crystals, melting point 144°–146° C.

(b) 5-(4-Chloro-3-cyclopentylsulfamoylphenyl)-5-hydroxy-1-methyl-2-oxopyrrolidine is obtained analogously to the instructions indicated in Example 1 from 6.5 g of 4-(4-chloro-3-cyclopentylsulfamoylphenyl)-4-oxobutanoic acid and 40 ml of 40% strength aqueous methylamine solution using 2.6 ml of triethylamine and 1.8 ml of ethyl chloroformate.

Colorless crystals, melting point 136°–139° C.

EXAMPLE 23

5-(4-Chloro-3-cyclohexylsulfamoylphenyl)-5-hydroxy-1-methyl-2-oxopyrrolidine (a) 4-(4-Chloro-3-cyclohexylsulfamoylphenyl)-4-oxobutanoic acid is obtained analogously to the instructions indicated in Example 15(a) from 9.3 g of 4-(4-chloro-3-chlorosulfonylphenyl)-4-oxobutanoic acid and 9 g of cyclohexylamine.

Melting point 133°–134° C.

(b) 5-(4-Chloro-3-cyclohexylsulfamoylphenyl)-5-hydroxy-1-methyl-2-oxopyrrolidine is obtained analogously to the instructions indicated in Example 1 from 6 g of 4-(4-chloro-3-cyclohexylsulfamoylphenyl)-4-oxobutanoic acid and 40 ml of 40% strength aqueous methylamine solution using 1.8 ml of ethyl chloroformate and 2.5 ml of triethylamine, the mixture being worked up according to the instructions indicated in Example 5.

Colorless crystals, melting point 148°–150° C.

EXAMPLE 24

5-(4-Chloro-3-dipropylsulfamoylphenyl)-5-hydroxy-1-methyl-2-oxopyrrolidine (a) 4-(4-Chloro-3-dipropylsulfamoylphenyl)-4-oxobutanoic acid is obtained analogously to the instructions indicated in Example 15(a) from 9.3 g of 4-(4-chloro-3-chlorosulfonylphenyl)-4-oxobutanoic acid and 10 g of dipropylamine.

Colorless crystals, melting point 100°–102° C.

(b) 5-(4-Chloro-3-dipropylsulfamoylphenyl)-5-hydroxy-1-methyl-2-oxopyrrolidine is obtained analogously to the instructions indicated in Example 1 from 7.5 g of 4-(4-chloro-3-dipropylsulfamoylphenyl)-oxobutanoic acid and 100 ml of 40% strength aqueous methylamine solution using triethylamine and ethyl chloroformate.

Melting point 110°–114° C.

EXAMPLE 25

5-(4-Chloro-3-dimethylsulfamoylphenyl)-5-hydroxy-1-methyl-2-oxopyrrolidine (a) 4-(4-Chloro-3-dimethylsulfamoylphenyl)-4-oxobutanoic acid is obtained analogously to the instructions indicated in Example 15(a) from 15.5 g of 4-(4-chloro-3-chlorosulfonylphenyl)-4-oxobutanoic acid and a solution of 10 g of dimethylamine in 150 ml of methanol.

Colorless crystals, melting point 114°–116° C.

(b) Methyl 4-(4-chloro-3-dimethylsulfamoylphenyl)-4-oxobutanoate is obtained analogously to the instructions described in Example 2(a) from 4-(4-chloro-3-dimethylsulfamoylphenyl)-4-oxobutanoic acid and methanol in the presence of acetyl chloride.

Colorless crystals, melting point 55°–56° C.

(c) 5-(4-Chloro-3-dimethylsulfamoylphenyl)-5-hydroxy-1-methyl-2-oxopyrrolidine is obtained analogously to the instructions indicated in Example 2(b) from 8.8 g of methyl 4-(4-chloro-3-dimethylsulfamoylphenyl)-4-oxobutanoate and a solution of 6 g of methylamine in 100 ml of methanol.

Colorless crystals, melting point 128°–131° C.

EXAMPLE 26

5-[4-Chloro-3-(2-phenylethylsulfamoyl)-phenyl]-5-hydroxy-1-methyl-2-oxopyrrolidine (a) 4-[4-Chloro-3-(2-phenylethylsulfamoyl)-phenyl]-4-oxobutanoic acid is obtained by adding 10 g of 4-(4-chloro-3-chlorosulfonylphenyl)-4-oxobutanoic acid to a solution of 5.45 g of 2-phenylethylamine and 8.11 g of triethylamine at room temperature in the course of 12 hours, whilst cooling with ice and stirring, acidifying the mixture with HCl and crystallizing the amorphous precipitate under fresh water in the course of 30 to 40 hours. The liquid is decanted off, a little methanol is added to the residue and, after stirring for one hour, the crystals are filtered off.

Melting point 147°–149° C.

(b) 5-[4-Chloro-3-(2-phenylethylsulfamoyl)-phenyl]-5-hydroxy-1-methyl-2-oxopyrrolidine is obtained analogously to the instructions indicated in Example 1 from 4.6 g of 4-[4-chloro-3-(2-phenylethylsulfamoyl)-phenyl]-4-oxobutanoic acid, 1.6 ml of triethylamine and 1.2 ml of ethyl chloroformate, melting point 149°–153° C.

EXAMPLE 27

5-(4-Chloro-3-N-benzyl-N-methylsulfamoylphenyl)-5-hydroxy-1-methyl-2-oxopyrrolidine (a) 4-(4-Chloro-3-N-benzyl-N-methylsulfamoylphenyl)-4-oxobutanoic acid is obtained analogously to the instructions indicated in Example 26(a) from 10 g of 4-(4-chloro-3-chlorosulfonylphenyl)-4-oxobutanoic acid, 5.4 g of N-methyl-N-benzylamine and 8.1 g of triethylamine in methanol.

Melting point 73° C.

(b) 5-(4-Chloro-3-N-benzyl-N-methylsulfamoylphenyl)-5-hydroxy-1-methyl-2-oxopyrrolidine is obtained analogously to the instructions indicated in Example 1 from 7 g of 4-(4-chloro-3-N-benzyl-N-methylsulfamoylphenyl)-4-oxobutanoic acid and 60 ml of 40% strength aqueous methylamine solution using 2.4 ml of triethylamine and 1.8 ml of ethyl chloroformate.

Colorless crystals, melting point 116°–119° C.

EXAMPLE 28

5-[4-Chloro-3-(2,4-dimethoxybenzylsulfamoyl)-phenyl]-5-hydroxy-1-methyl-2-oxopyrrolidine (a) 4-[4-Chloro-3-(2,4p-dimethoxybenzylsulfamoyl)-phenyl]-4-oxobutanoic acid is obtained analogously to the instruction 26(a) from 9.4 g of 4-(4-chloro-3-chlorosulfonylphenyl)-4-oxobutanoic acid, 5.4 g of 2,4-dimethoxybenzylamine and 8.5 g of triethylamine.

Melting point 167° C.

(b) 5-[4-Chloro-3-(2,4-dimethoxybenzylsulfamoyl)-phenyl]-5-hydroxy-1-methyl-2-oxopyrrolidine is obtained analogously to the intructions indicated in Example 1 from 6.6 g of 4-[4-chloro-3-(2,4-dimethoxybenzylsulfamoyl)-phenyl]-4-oxobutanoic acid and 80 ml of aqueous 40% strength methylamine solution using 1.7 ml of ethyl chloroformate and 2.4 ml of triethylamine.

Colorless crystals, melting point 164°–166° C.

EXAMPLE 29

5-[4-Chloro-3-(2-methoxy-1-propylsulfamoyl)-phenyl]-5-hydroxy-1-methyl-2-oxopyrrolidine (a) 4-[4-Chloro-3-(2-methoxy-1-propylsulfamoyl)-phenyl]-4-oxobutanoic acid is obtained analogously to the instructions indicated for Example 15(a) from 10 g of 4-(4-chloro-3-chlorosulfonylphenyl)-4-oxobutanoic acid and 9.7 g of 2-methoxy-1-propylamine.

Melting point 121° C.

(b) 5-[4-Chloro-3-(2-methoxy-1-propylsulfamoyl)-phenyl]-5-hydroxy-1-methyl-2-oxopyrrolidine is obtained analogously to the instructions indicated in Example 1 from 8 g of 4-[4-chloro-3-(2-methoxy-1-propylsulfamoyl)-phenyl]-4-oxobutanoic acid, 3 ml of triethylamine and 2.2 ml of ethyl chloroformate. Melting point 124°–126° C.

EXAMPLE 30

5-[3-(2,2-Diethoxyethylsulfamoyl)-4-chlorophenyl]-5-hydroxy-1-methyl-2-oxopyrrolidine (a) 4-[3-(2,2-Diethoxyethylsulfamoyl)-4-chlorophenyl]-4-oxobutanoic acid is obtained analogously to the instructions indicated in Example 15(a) from 13.4 g of aminoacetaldehyde diethyl acetal and 9.4 g of 4-(4-chloro-3-chlorosulfonylphenyl)-4-oxobutanoic acid.

Melting point 142° C.

(b) 5-[3-(2,2-Diethoxyethylsulfamoyl)-4-chlorophenyl]-5-hydroxy-1-methyl-2-oxopyrrolidine is obtained analogously to the instructions indicated in Example 1 from 8.1 g of 4-[3-(2,2-diethoxyethylsulfamoyl)-4-chlorophenyl]-4-oxobutanoic acid and 100 ml of 40% strength aqueous methylamine solution using 3.2 ml of triethylamine and 2.2 ml of ethyl chloroformate.

Colorless crystals, melting point 135°–138° C.

EXAMPLE 31

5-[4-Chloro-3-(2-chlorobenzylsulfamoyl)-phenyl]-5-hydroxy-1-methyl-2-oxopyrrolidine (a) 4-[4-Chloro-3-(2-chlorobenzylsulfamoyl)-phenyl]-4-oxobutanoic acid is obtained analogously to the instructions indicated in Example 26a) from 9.4 g of 4-(4-chloro-3-chlorosulfonylphenyl)-4-oxobutanoic acid, 5 g of 2-chlorobenzylamine and 8.5 g of triethylamine. Melting point 158° C.

(b) 5-[4-Chloro-3-(2-chlorobenzylsulfamoyl)-phenyl]-5-hydroxy-1-methyl-2-oxopyrrolidine is obtained analogously to the instructions indicated in Example 1 from 6.3 g of 4-[4-chloro-3-(2-chlorobenzylsulfamoyl)-phenyl]-4-oxobutanoic acid and 75 ml of aqueous 40% strength methylamine solution using 2.4 ml of triethylamine and 1.7 ml of ethyl chloroformate. Melting point 144°-145° C.

EXAMPLE 32

5-(4-Chloro-3-sulfamoylphenyl)-5-hydroxy-1-methyl-2-oxopyrrolidine or
4-(4-chloro-3-sulfamoylphenyl)-4-oxobutanoic acid methylamide (a) 4-(4-Chloro-3-sulfamoylphenyl)-4-oxobutanoic acid N-benzyl-N-methylamide is obtained analogously to the instructions indicated in Example 1 from 7.3 g of 4-(4-chloro-3-sulfamoylphenyl)-3-oxobutanoic acid and 3.2 g of N-benzyl-N-methylamine using 3.8 ml of triethylamine and 2.6 ml of ethyl chloroformate. Colorless crystals from ethyl acetate, melting point 162° C.

(b) 2 g of 4-(4-chloro-3-sulfamoylphenyl)-4-oxobutanoic acid N-benzyl-N-methylamide are hydrogenated in the presence of 0.5 g of palladium black in 40 ml of methanol in a duck-shaped shaking vessel until the theoretical amount of hydrogen has been taken up, the catalyst is filtered off, the filtrate is concentrated and the residue is worked up analogously to the instructions 1, to give 5-(4-chloro-3-sulfamoylphenyl)-5-hydroxy-1-methyl-2-oxopyrrolidine. Melting point 147°-149° C.

EXAMPLE 33

5-(4-Chloro-3-dimethylsulfamoylphenyl)-5-hydroxy-1-methyl-2-oxopyrrolidine or
4-(4-chloro-3-dimethylsulfamoylphenyl)-5-oxobutanoic acid methylamide 14.9 g of 5-bromo-2-chlorobenzenesulfonic acid dimethylamide in 100 ml of absolute tetrahydrofuran are slowly added dropwise to an intensively stirred solution of 0.05 mole of butyl-lithium in 150 ml of absolute tetrahydrofuran at −45° C., with the exclusion of oxygen and atmospheric moisture, and the mixture is stirred at −40° C. for a further 20 to 30 minutes. A solution of 5 g of N-methylsuccinimide in about 150 ml of absolute tetrahydrofuran is added dropwise to the resulting solution of 4-chloro-3-dimethylsulfamoylphenyl-lithium in the course of about 45 minutes. The reaction mixture is then stirred overnight at room temperature and boiled under a reflux condenser for 1 to 2 hours. After cooling, the residue is broken up by adding 25 ml of saturated aqueous ammonium chloride solution, whilst cooling, the precipitate is filtered off and the filtrate is briefly dried over sodium sulfate. The solvent is driven off and the residue is crystallized under 70 to 100 ml of water. Colorless crystals, melting point 145°-147° C.

EXAMPLE 34

5-[4-Chloro-3-(1-pyrrolidinylsulfonyl)-phenyl]-5-hydroxy-1-methyl-2-oxopyrrolidine or
4-[4-chloro-3-(1-pyrrolidinylsulfonyl)phenyl]-4-oxobutanoic acid N-methylamide is obtained analogously to the instructions indicated in Example 1 from 7 g of
4-[4-chloro-3-(1-pyrrolidinylsulfonyl)-phenyl]-4-oxobutanoic acid and 40 ml of 40% strength aqueous methylamine solution using 70 ml of tetrahydrofuran, 2.7 ml of triethylamine and 2.1 ml of ethyl chloroformate. Colorless crystals, melting point 182° C. (from isopropanol).

The 4-[4-chloro-3-(1-pyrrolidinylsulfonyl)-phenyl]-4-oxobutanoic acid used is obtained analogously to the instructions indicated in Example 26a) from 15.5 g of 4-(4-chloro-3-chlorosulfonylphenyl)-4-oxobutanoic acid and 10.8 g of pyrrolidine. Colorless crystals, melting point 142°-145° C.

EXAMPLE 35

5-[4-Chloro-3-(4-chlorobenzylsulfamoyl)-phenyl]-5-hydroxy-1-methyl-2-oxopyrrolidine or
4-[4-chloro-3-(4-chlorobenzylsulfamoyl)phenyl]-4-oxobutanoic acid N-methylamide is obtained analogously to the instructions indicated in Example 1 from 8.4 g of
4-[4-chloro-3-(4-chlorobenzyl-sulfamoyl)-phenyl]-4-oxobutanoic acid and 100 ml of 40% strength aqueous methylamine solution using 100 ml of tetrahydrofuran, 3.2 ml of triethylamine and 2.2 ml of ethyl chloroformate. Colorless crystals from isopropanol, melting point 179° C.

The 4-[4-chloro-3-(4-chlorobenzylsulfamoyl)-phenyl]-4-oxobutanoic acid is obtained analogously to the instructions indicated in Example 26a) from 9.4 g of 4-(4-chloro-3-chlorosulfonylphenyl)-4-oxobutanoic acid, 5 g of 4-chlorobenzylamine and 8.5 g of triethylamine in 150 ml of methanol. Colorless crystals, melting point 158° C.

EXAMPLE 36

5-(4-Chloro-3-cyclopropylsulfamoylphenyl)-5-hydroxy-1-methyl-2-oxopyrrolidine or
4-(4-chloro-3-cyclopropylsulfamoylphenyl)-4-oxobutanoic acid N-methylamide is obtained analogously to the instructions indicated in Example 1 from 8 g of
4-(4-chloro-3-cyclopropylsulfamoyl-phenyl)-4-oxobutanoic acid and 50 ml of 40% strength methylamine solution (aqueous) using 3.3 ml of triethylamine and 2.4 ml of ethyl chloroformate in 80 ml of tetrahydrofuran. Colorless crystals from isopropanol, melting point 184°-185° C.

The 4-(4-chloro-3-cyclopropylsulfamoylphenyl)-4-oxobutanoic acid is obtained analogously to the instructions indicated in Example 26a) from 10 g of 4-(4-chloro-3-chlorosulfonylphenyl)-4-oxobutanoic acid, 2.5 g of cyclopropylamine, 8 g of triethylamine and 150 ml of methanol. Colorless crystals, melting point 135° C.

EXAMPLE 37

5-(4-Chloro-3-cyclooctylsulfamoylphenyl)-5-hydroxy-1-methyl-2-oxopyrrolidine or 4-(4-chloro-3-cyclooctyl-sulfamoylphenyl)-4-oxobutanoic acid N-methylamide is obtained analogously to the instructions indicated in Example 1 from 4.8 g of 4-(4-chloro-3-cyclooctylsulfamoylphenyl)-4-oxobutanoic acid, 40 ml of 40% strength aqueous methylamine solution using 1.2 ml of ethyl chloroformate and 1.6 ml of triethylamine in 50 ml of absolute tetrahydrofuran.

Colorless solid, melting point 112° C.

The 4-(4-chloro-3-cyclooctylsulfamoylphenyl)-4-oxobutanoic acid is obtained analogously to the instructions indicated in Example 26a) from 4-(4-chloro-3-chlorosulfonylphenyl)-4-oxobutanoic acid, cyclooctylamine and triethylamine.

Colorless crystals, melting point 127° C.

EXAMPLE 38

5-(4-Chloro-3-cyclododecylsulfamoylphenyl)-5-hydroxy-1-methyl-2-oxopyrrolidine or 4-(4-chloro-3-cyclododecylsulfamoylphenyl)-4-oxobutanoic acid N-methylamide is obtained analogously to the instructions indicated in Example 1 from 6.4 g of 4-(4-chloro-3-cyclododecylsulfamoylphenyl)-4-oxobutanoic acid, 1.9 ml of triethylamine, 1.61 ml of ethyl chloroformate and 50 ml of a 40% strength aqueous methylamine solution. Colorless crystals from isopropanol, melting point 192° C.

The 4-(4-chloro-3-cyclododecylsulfamoyl-phenyl)-4-oxobutanoic acid is obtained analogously to the instructions indicated in Example 26a) from 4-(4-chloro-3-chlorosulfonylphenyl)-4-oxobutanoic acid, cyclododecylamine and triethylamine. Colorless crystals from water/glacial acetic acid, melting point 140° C.

EXAMPLE 39

5-[4-Chloro-3-(4-methylbenzylsulfamoyl)-phenyl]-5-hydroxy-1-methyl-2-oxopyrrolidine or 4-[4-chloro-3-(4-methylbenzylsulfamoyl)-phenyl]-4-oxobutanoic acid N-methylamide is obtained analogously to the instructions indicated in Example 1 from 4.3 g of 4-[4-chloro-3-(4-methylbenzylsulfamoyl)-phenyl]-4-oxobutanoic acid and 50 ml of 40% strength aqueous methylamine solution using 50 ml of tetrahydrofuran, 1.6 g of triethylamine and 1.1 ml of ethyl chloroformate. Colorless crystals.

The 4-[4-chloro-3-(4-methylbenzylsulfamoyl)-phenyl]-4-oxobutanoic acid is obtained analogously to the instructions indicated in Example 26a) from 9.4 g of 4-(4-chloro-3-chlorosulfonylphenyl)-4-oxobutanoic acid, 4.3 g of 4-methylbenzylamine and 8.5 g of triethylamine in 150 ml of methanol. Melting point 129°-131° C.

EXAMPLE 40

5-(3-Benzylsulfamoyl-4-chlorophenyl)-5-hydroxy-1-methyl-2-oxopyrrolidine or 4-(3-benzylsulfamoyl-4-chlorophenyl)-4-oxobutanoic acid N-methylamide is obtained analogously to the instructions indicated in Example 1 from 9.5 g of 4-(3-benzylsulfamoyl-4-chlorophenyl)-4-oxobutanoic acid and 100 ml of 40% strength aqueous methylamine solution using 100 ml of tetrahydrofuran, 4 ml of triethylamine and 2.75 ml of ethyl chloroformate. Colorless crystals, melting point 134°-136° (from isopropanol).

The 4-(3-benzylsulfamoyl-4-chlorophenyl)-4-oxobutanoic acid is obtained analogously to the instructions indicated in Example 26a) from 15.5 g of 4-(4-chloro-3-chlorosulfonylphenyl)-4-oxobutanoic acid and 15 g of benzylamine in methanol. Colorless crystals, melting point 153° C.

EXAMPLE 41

5-[4-Chloro-3-(1-pyrrolidinylsulfonyl)-phenyl]-5-hydroxy-1-methyl-2-oxopyrrolidine or 4-[4-chloro-3-(1-pyrrolidinylsulfonyl)-phenyl]-4-oxobutanoic acid N-methylamide (a) 3.9 g of 4-[4-chloro-3-(1-pyrrolidinylsulfonyl)-phenyl]-4-oxobutanoic acid are boiled under a reflux condenser in 50 ml of acetic anhydride for 1 hour, the solvent is driven off under reduced pressure and the residue is caused to crystallize under diisopropyl ether. 5-[4-Chloro-3-(1-pyrrolidinylsulfonyl)-phenyl]-2,3-dihydro-3-oxofuran is obtained in the form of light red-colored crystals of melting point 108°-111° C.

(b) 2.8 g of 5-[4-chloro-3-(1-pyrrolidinylsulfonyl)-phenyl]-4-oxobutanoic acid are stirred in 40 ml of 40% strength aqueous methylamine solution at room temperature for 16 hours, the solvent is distilled off under reduced pressure and 15-20 ml of water are added to the residue. The pH is adjusted to 7 with 2 N HCl and the crystals are filtered off.

Colorless crystals, melting point 184° C.

EXAMPLE 42

5-(4-Chloro-3-n-octylsulfamoylphenyl)-5-hydroxy-1-methyl-2-oxo-pyrrolidine or 4-(4-chloro-3-n-octylsulfamoylphenyl)-4-oxobutanoic acid N-methylamide is obtained analogously to the instructions indicated in Example 1 from 8 g of 4-(4-chloro-3-n-octylsulfamoylphenyl)-4-oxobutanoic acid using 2.2 ml of chloroformic acid ethyl ester, 3.2 ml of triethylamine, 100 ml of 40% strength aqueous methylamine solution and 100 ml of tetrahydrofuran. Crystals slowly separate in methanol, melting point 126°-128° C.

The 4-(4-chloro-3-n-octylsulfamoylphenyl)-4-oxobutanoic acid is obtained as described in Example 15a) from 9.4 g of 4-(4-chloro-3-chlorosulfonylphenyl)-4-oxobutanoic acid, 13 g of n-octylamine and 150 ml of methanol, melting point 83°-85° C.

EXAMPLE 43

5-(4-Chloro-3-cyclohexylmethylsulfamoylphenyl)-5-hydroxy-1-methyl-2-oxopyrrolidine or 4-(4-chloro-3-cyclohexylmethylsulfamoylphenyl)-4-oxobutanoic acid N-methylamide is obtained analogously to the instructions indicated in Example 1 from 6.9 g of 4-(4-chloro-3-cyclohexylmethylsulfamoylphenyl)-4-oxobutanoic acid in 70 ml of absolute tetrahydrofurane using 2.4 ml of triethylamine, 1.8 ml of ethyl chloroformate and 80 ml of 40% strength aqueous methylamine solution. After extraction of the aqueous phase with ethyl acetate and drying over $Na_2SO_4$, the organic phase is concentrated and the residue is crystallized with the use of diisopropyl ether. Colorless crystals, melting point 138°–140° C.

The 4-(4-chloro-3-cyclohexylmethylsulfamoylphenyl)-4-oxobutanoic acid is obtained as described in Example 26a) from 10 g of 4-(4-chloro-3-chlorosulfonylphenyl)-4-oxobutanoic acid, 5.1 g of aminomethylcyclohexane and 8 g of triethylamine in methanol. Colorless crystals, melting point 134°–137° C.

EXAMPLE 44

5-Hydroxy-1-methyl-5-(4-methyl-3-sulfamoylphenyl)-2-oxopyrrolidine or 4-(4-methyl-3-sulfamoylphenyl)-4-oxobutanoic acid N-methylamide (a) 10 g of 4-(4-methylphenyl)-4-oxobutanoic acid are introduced at −15° C. into 100 ml of 100% strength nitric acid (d=1.52), the mixture is stirred for 10 minutes at the indicated temperature and the crystalline 4-(4-chloro-3-nitrophenyl)-4-oxobutanoic acid is filtered off. Melting point 143°–145° C. (from water/ethanol).

(b) In a mixture of 350 ml of methanol and 85 ml of dioxane 35 g of 4-(4-chloro-3-nitrophenyl)-4-oxobutanoic acid are hydrogenated under 40 atmospheres and at 50° C. with Raney nickel and hydrogen. After concentration, the 4-(3-amino-4-methyl-phenyl)-4-oxobutanoic acid (melting point 102°–105°) is allowed to crystallize in 350 ml of water.

(c) After addition of 33 ml of 2 N HCl, 3.7 g of 4-(3-amino-4-methylphenyl)-4-oxobutanoic acid are diazotized at 0° C. with a solution of 1.2 g of sodium nitrite in 6.5 ml of water and the solution is poured in portions into a mixture of 1.1 g of $CuCl_2 \times 2$ $H_2O$ and 20 ml of glacial acetic acid solution saturated with $SO_2$. The mixture is stirred for 30 minutes at 16°–18° C., 100 ml of $H_2O$ are added, stirring is continued for a further 30 minutes at 0°–5° C. and the crystalline 4-(3-chlorosulfonyl-4-methylphenyl)-4-oxobutanoic acid (melting point 116°–119° C.) is filtered off.

(d) 10 g 4-(3-chlorosulfonyl-4-methylphenyl)-4-oxobutanoic acid are introduced into 70 ml of liquid ammonia. After evaporation at room temperature, the residue is taken up in 70 ml of water, the pH is adjusted to 1–2 with 2 N HCl and the crystalline 4-(4-methyl-3-sulfamoylphenyl)-4-oxobutanoic acid, melting point 165° C. is filtered off.

(e) 9.4 g of 4-(4-methyl-3-sulfamoylphenyl)-4-oxobutanoic acid are reacted analogously to the instructions indicated in Example 1 using 64 ml of absolute tetrahydrofurane, 6.7 ml of triethylamine, 4.7 ml of ethyl chloroformate and 90 ml of 40% strength aqueous methylamine solution to yield 5-hydroxyl-1-methyl-5-(4-methyl-3-sulfamoylphenyl)-2-oxopyrrolidine.

Colorless crystals from a small amount of acetonitrile, melting point 124° C.

EXAMPLE 45

5-Hydroxy-1-methyl-2-oxo-5-(3-di-n-propylsulfamoylphenyl)pyrrolidine or 4-oxo-4-(2-di-n-propylsulfamoylphenyl)butanoic acid N-methylamide (a) 4-(3-Chlorosulfonylphenyl)-4-oxobutanoic acid is obtained analogously to the instructions indicated in Example 44c) from 4-(3-aminophenyl)-4-oxobutanoic acid (colorless crystals, melting point 136°–138° C.) and is transformed, in the manner described in Example 15a) with di-n-propylamine into 4-oxo-4-(3-di-n-propylsulfamoylphenyl)-butanoic acid, melting point 73°–78° C.

(b) 5-Hydroxy-1-methyl-2-oxo-5-(3-di-n-propylsulfamoylphenyl)-pyrrolidine is obtained analogously to the instructions indicated in Example 1 from 6.8 g of 4-oxo-4-(3-di-n-propylsulfamoylphenyl)-butanoic acid using 100 ml of absolute tetrahydrofuran, 3.2 ml of triethylamine, 2.2 ml of ethyl chloroformate and 100 ml of 40% strength aqueous methylamine solution. Colorless crystals, melting point 58°–60° C.

EXAMPLE 46

5-(4-Chloro-3-di-n-propylsulfamoylphenyl)-5-hydroxy-1-methyl-2-oxopyrrolidine or 4-(4-chloro-3-di-n-propylsulfamoylphenyl)-4-oxobutanoic acid N-methylamide is obtained analogously to Example 41 from 5-(4-chloro-3-di-n-propylsulfamoylphenyl)-2,3-dihydro-2-oxofurane and 40% strength aqueous methylamine solution. Colorless crystals, melting point 112°–114° C.

The 5-(4-chloro-3-di-n-propylsulfamoylphenyl)-2,3-di-hydro-2-oxofurane (melting point 118°–121° C.) is prepared as described in Example 41a) from 4-(4-chloro-3-di-n-propylsulfamoyl)-4-oxobutanoic acid and acetanhydride.

EXAMPLE 47

5-(4-Chloro-3-methylsulfamoylphenyl)-5-hydroxy-1-methyl-2-oxopyrrolidine 2.1 g of triethylamine are rapidly added dropwise to a mixture of 6.2 g 4-(4-chloro-3-chlorosulfonylphenyl)-4-oxobutanoic acid and 2.2 g of ethyl chloroformate in 20 ml of absolute tetrahydrofurane at a rate such that the internal temperature is maintained between −5° and −10° C. The mixture is stirred for about 5 to 10 minutes at −5° to 0° C. and 1.55 ml of a 4% strength solution of gaseous methylamine in tetrahydrofurane is rapidly added dropwise. Stirring is continued for 15 to 20 minutes at 10°–15° C., the reaction mixture is poured into water and extracted twice, each time with 80 ml of ethyl acetate. The organic phase is washed once with 50 ml of 0.01 N hydrochloric acid at 0° C. and once with cold bicarbonate solution, dried for one hour over $Na_2SO_4$ at 0°–10° C. while stirring with a magnetic stirrer and concentrated on a rotavapor (bath temperature ≦30° C.). The 5-(4-chloro-3-chlorosulfonylphenyl)-5-hydroxy-1-methyl-2-oxo-pyrrolidine is mostly obtained in the form of an amorphous residue. After addition of 20 ml of 40% strength aqueous methylamine solution (cooling) the mixture is stirred overnight at room temperature, concentrated and allowed to crystallize under water. Colorless crystals, melting point 112°–114° C. (from ethanol).

EXAMPLE 48

5-(4-Chloro-3-di-n-propylsulfamoylphenyl)-5-hydroxy-1-methyl-2-oxopyrrolidine is obtained by stirring the 5-(4-chloro-3-chlorosulfonylphenyl)-5-hydroxy-1-methyl-2-oxopyrrolidine obtained as described in Example 47 in a solution of 5 g of di-n-propylamine in 40 ml of methanol for 14 hours at room temperature.

After concentration, the residue is worked up as described in Example 1.

Colorless crystals, melting point 111°–113° C.

We claim:

1. A benzenesulfonamide derivative of the formula I

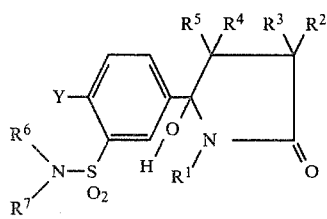

and in its tautomeric form of the formula

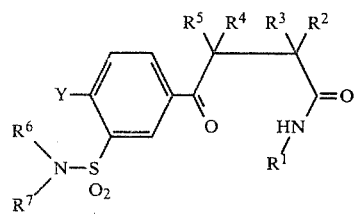

in which $R^1$ denotes hydrogen, alkyl of 1 to 4 carbon atoms, alkenyl of 2 to 4 carbon atoms, alkyl of 1 to 4 C atoms substituted with a methoxy group, cycloalkyl of 3 to 5 ring members or benzyl; $R^2$ to $R^6$ denote hydrogen, or an alkyl radical of 1 to 4 C atoms; $R^7$ denotes hydrogen, alkyl of 1 to 10 C atoms, alkyl radical of 1 to 10 C atoms substituted with one to two methoxy groups, an ethylenedioxy, or propylenedioxy group, alkenyl of 3 to 5 C atoms, cycloalkyl of 3 to 12 ring members, or cycloalkyl of 3 to 12 ring members substituted with a methyl group, cycloalkylalkyl of 5 or 6 ring members of 1 or 2 C atoms in the alkyl moiety thereof, phenylalkyl of 1 to 2 C atoms in the alkyl moiety thereof, monosubstituted or disubstituted phenylalkyl of 1 to 2 C atoms in the alkyl moiety thereof wherein the substituent is methyl, methoxy or chlorine; or $R^6$ and $R^7$, joined together with the N atom denote a saturated 5-membered to 6-membered heterocyclic ring and Y denotes hydrogen, methyl, halogen, or trifluoromethyl.

2. 5-(4-Chloro-3-sulfamoylphenyl)-5-hydroxy-1-methyl-2-oxopyrrolidine or 4-(4-chloro-3-sulfamoylphenyl)-4-oxobutanoic acid methylamide.

3. 5-(4-Bromo-3-sulfamoylphenyl)-5-hydroxy-1-methyl-2-oxopyrrolidine or 4-(4-bromo-3-sulfamoylphenyl)-4-oxobutanoic acid methylamide.

4. 5-(4-Chloro-3-methylsulfamoylphenyl)-5-hydroxy-1-methyl-2-oxopyrrolidine or 4-(4-chloro-3-methylsulfamoylphenyl)-4-oxobutanoic acid methylamide.

5. 5-(4-Chloro-3-propylsulfamoylphenyl)-5-hydroxy-1-methyl-2-oxopyrrolidine or 4-(4-chloro-3-propylsulfamoylphenyl)-4-oxobutanoic acid methylamide.

6. 5-(3-Allylsulfamoyl-4-chlorophenyl)-5-hydroxy-1-methyl-2-oxopyrrolidine or 4-(3-allylsulfamoyl-4-chlorophenyl)-4-oxobutanoic acid methylamide.

7. 5-(4-Chloro-3-isobutylsulfamoylphenyl)-5-hydroxy-1-methyl-2-oxopyrrolidine or 4-(4-chloro-3-isobutylsulfamoylphenyl)-4-oxobutanoic acid methylamide.

8. 5-(4-Chloro-3-sec.-butylsulfamoylphenyl)-5-hydroxy-1-methyl-2-oxopyrrolidine or 4-(4-chloro-3-sec.-butylsulfamoylphenyl)-4-oxobutanoic acid methylamide.

9. 5-(4-Chloro-3-hexylsulfamoylphenyl)-5-hydroxy-1-methyl-2-oxopyrrolidine or 4-(4-chloro-3-hexylsulfamoylphenyl)-4-oxobutanoic acid methylamide.

10. 5-(4-Chloro-3-dimethylsulfamoylphenyl)-5-hydroxy-1-methyl-2-oxopyrrolidine or 4-(4-chloro-3-dimethylsulfamoylphenyl)-4-oxobutanoic acid methylamide.

11. 5-(4-Chloro-3-dipropylsulfamoylphenyl)-5-hydroxy-1-methyl-2-oxopyrrolidine or 4-(4-chloro-3-dipropylsulfamoylphenyl)-4-oxobutanoic acid methylamide.

12. A benzenesulfonamide derivative of the general formula I

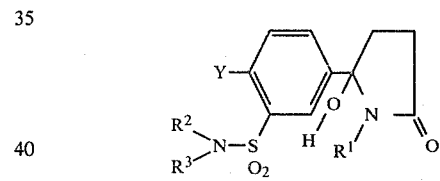

and in its tautomeric form Ia

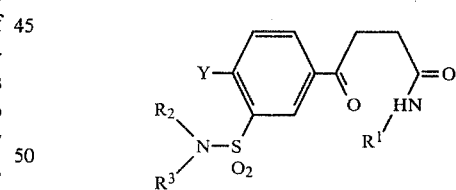

in which $R^1$ is hydrogen, alkyl with 1 to 4 carbon atoms or allyl, $R^2$ is hydrogen or alkyl of 1 to 4 carbon atoms, $R^3$ is hydrogen, alkyl of 1 to 10 carbon atoms, allyl, cycloalkyl with 3 to 8 ring members, benzyl and benzyl in which the phenyl ring thereof may be monosubstituted with methyl or chlorine and Y is halogen or methyl.

13. A pharmaceutical formulation in a therapeutic unit dosage from 0.5 to 500 mg and an adjuvant and/or a pharmaceutically acceptable carrier therefor which comprises as an essential component a compound as defined in claim 1.

14. A pharmaceutical formulation which essentially contains a compound as defined in claim 1 in a unit dosage form of 0.5 to 500 mg.

* * * * *